US008211883B2

(12) United States Patent
Cooper et al.

(10) Patent No.: US 8,211,883 B2
(45) Date of Patent: Jul. 3, 2012

(54) TOPICAL DELIVERY OF PHTHALOCYANINES

(75) Inventors: Kevin D. Cooper, Moreland Hills, OH (US); Nancy L. Oleinick, University Heights, OH (US); Malcolm E. Kenney, Cleveland Heights, OH (US); Thomas S. McCormick, Orange Village, OH (US); Jeffrey C. Berlin, Clayville, NY (US); Elma D. Baron, Concord, OH (US)

(73) Assignee: Case Western Reserve University, Cleveland, OH (US)

( * ) Notice: Subject to any disclaimer, the term of this patent is extended or adjusted under 35 U.S.C. 154(b) by 866 days.

(21) Appl. No.: 10/599,433

(22) PCT Filed: Apr. 1, 2005

(86) PCT No.: PCT/US2005/011381
§ 371 (c)(1),
(2), (4) Date: Sep. 19, 2008

(87) PCT Pub. No.: WO2005/099689
PCT Pub. Date: Oct. 27, 2005

(65) Prior Publication Data
US 2009/0156552 A1 Jun. 18, 2009

Related U.S. Application Data

(60) Provisional application No. 60/559,293, filed on Apr. 1, 2004.

(51) Int. Cl.
*A01N 55/02* (2006.01)
*C07B 47/00* (2006.01)
*C07D 487/22* (2006.01)
(52) U.S. Cl. .................. 514/185; 540/145; 514/410
(58) Field of Classification Search .................. 540/145; 514/185, 410
See application file for complete search history.

(56) References Cited

U.S. PATENT DOCUMENTS 5,358,940 A * 10/1994 Capraro et al. .................. 514/63

FOREIGN PATENT DOCUMENTS

| EP | 0633024 | * | 6/1994 |
| EP | 0 633 024 | | 1/1995 |
| EP | 0720853 | * | 12/1995 |
| EP | 0 720 853 | | 7/2001 |
| WO | 92/01753 | | 2/1992 |
| WO | WO 92/01753 | * | 2/1992 |
| WO | 95/06688 | | 3/1995 |
| WO | WO 95/06688 | * | 3/1995 |
| WO | 99/23882 | | 5/1999 |
| WO | WO 02/096913 | * | 5/2002 |
| WO | 02/096913 | | 12/2002 |
| WO | 03/037902 | | 5/2003 |

OTHER PUBLICATIONS

Vorozhtsov et al., CHem Abstacts 2002., vol. 136.*
XP-002211842; Vorozhtsov, G. N. et al; Phosphonylmethyl Phthalocyanine Derivatives in Preparations for Photodynamic Therapy; Chemical Abstracts, vol. 136, No. 183942, 2002.
XP-002346530; Wainwright, M; Local Treatment of Viral Disease Using Photodynamic Therapy; International Journal of Antimicrobial Agents; vol. 21, 2003, pp. 510-520.
E. Ben-Hur et al; The phthalocyanines: A New Class of Mammalian Cells Photosensitizers with a Potential for Cancer Phototherapy; Int. J. Radiat. Biol.; vol. 47, No. 2, pp. 145-147, 1985.
C.M. Allen et al; Current status of Phthalocyanines in the Photodynamic Therapy of Cancer; Journal of Porphyrins and Phthalocyanines 5; pp. 161-169; 2001.
E. Ben-Hur et al; Phthalocyanines in Photobiology and Their Medical Applications; The Porphyrin Handbook; vol. 19; Applications of Phthalocyanines; Elsevier Science; pp. 1-35; 2003.
C.D. Abernathey et al; Activity of Phthalocyanine Photosensitizers Against Human Glioblastoma in Vitro; Neurosurgery, vol. 21, No. 4; pp. 468-473; 1987.
W.S. Chan et al; Tissue Uptake, Distribution, and Potency of the Photoactivatable Dye Chloroaluminum Sulfonated Phthalocyanine in Mice Bearing Transplantable Tumors; Cancer Research 48, 3040-3044, 1988.
M. Sonoda; The Role of Singlet Oxygen in the Photohemolysis of Red Blood Cells Sensitized by Phthalocyanine Sulfonates; Photochemistry and Photobiology, vol. 46, No. 5; pp. 625-631; 1987.
N. Ramakrishnan et al; DNA Lesions and DNA Degradation in Mouse Lymphoma L5178Y Cells After Photodynamic Treatment Sensitized by Chloroaluminum Phthalocyanine; Photochemistry and Photobiology; vol. 50, No. 3; pp. 373-378, 1989.
M.L. Agarwai; Photodynamic Therapy Induces Rapid Cell Death by Apoptosis in L5178Y Mouse Lymphoma Cells; Cancer Research 51, 5993-5996, 1991.
Office Action from U.S. Appl. No. 12/408,116, dated Mar. 14, 2011.
Response to Office Action dated Mar. 14, 2011 from U.S. Appl. No. 12/408,116, filed May 11, 2011.
Office Action from U.S. Appl. No. 12/408,116, dated Jun. 28, 2011.
Response to Office Action dated Jun. 28, 2011 from U.S. Appl. No. 12/408,116, filed Sep. 2, 2011.
International Preliminary Report on Patentability from International Application No. PCT/US2005/011381, date of issuance of this report Oct. 4, 2006.
Vorozhtsov, GN et al: "Phosphonylmethyl phthalocyanine derivatives in preparations for photodynamic therapy" Chemical Abstracts 2002, vol. 136, Abstract No. 183942.

* cited by examiner

*Primary Examiner* — Paul V. Ward
(74) *Attorney, Agent, or Firm* — Calfee, Halter & Griswold LLP

(57) ABSTRACT

The invention relates to topical pharmaceutical compositions comprising a phthalocyanine, wherein a diamagnetic metal ion moiety is either coordinated or covalently bound to the phthalocyanine core. The invention also relates to methods for destroying cancer tissue, precancerous cells, photo-aged cells, damaged cells, or otherwise pathologic cells, or activated cells, such as lymphocytes or other cells of the immune system, or activated or inflamed tissue cells comprising topically administering to the cancer tissue or surrounding tissue an effective amount of a phthalocyanine composition.

20 Claims, 10 Drawing Sheets

TOPICAL DELIVERY OF PHTHALOCYANINES

This application is a national phase of International Application No. PCT/US2005/011381 filed Apr. 1, 2005 and published in the English language, and claims priority to U.S. Ser. No. 60/559,293 filed Apr. 1, 2004.

This work was supported by Federal Grant Nos. NIAMS-AR39750 and CA48735. The U.S. government may have certain rights in this invention.

FIELD OF INVENTION

The present invention is directed to topical pharmaceutical compositions comprising a series of novel phthalocyanines suitable for use as photosensitizers for photodynamic therapy. In addition, the present invention is directed to the methods of synthesizing these new compositions.

BACKGROUND OF THE INVENTION

Photodynamic therapy, hereinafter also referred to as "PDT", is a process for treating cancer wherein visible light is used to activate a substance, such as a dye or drug, which then attacks, through one or more photochemical reactions, the tumor tissue thereby producing a cell-killing, or cytotoxic, effect. It has been discovered that when certain non-toxic photodynamic sensitizers, such as hematoporphyrin derivative ("HpD" or "Photofrin® I") are applied to the human or animal body, they are selectively retained by the cancerous tissue while being eliminated by the healthy tissue.

The tumor or cancerous tissue containing the photosensitizer can then be exposed to therapeutic light of an appropriate wavelength and at a specific intensity for activation. The light can be directly applied through the skin to the cancerous area from a conventional light source (e.g., laser, sun lamp, white light sources with appropriate filters, etc.), or in cases where the cancerous tissue is located deeper within the body, through surgical or non-surgical entry such as by the use of fiber optic illumination systems, including flexible fiber optic catheters, endoscopic devices, etc. The light energy and the photosensitizer cause a photochemical reaction which kills the cell in which the photosensitizer resides.

Although the exact mechanisms of the photochemical reactions that kill the cancer cells are not clearly understood and vary depending upon the type of photosensitizer utilized, what is clear is that photodynamic therapy is effective for the preferential destruction of cancerous tissue. Furthermore, photodynamic therapy has several attractive features over conventional methods for treating cancer such as chemotherapy, radiation, surgical procedures, etc., in that the photosensitizers utilized are generally non-toxic, concentrate or remain preferentially in cancer cells, can be utilized with other modes of treatment since PDT does not generally interfere with other chemicals or processes, etc.

Considerable attention has recently been directed to a group of compounds having the phthalocyanine ring system. These compounds, called phthalocyanines, hereinafter also abbreviated as "Pc", are a group of photoactive dyes that are somewhat structurally similar (i.e., have a nitrogen-containing ring structure) to the porphyrin family. Phthalocyanines are azaporphyrins consisting of four benzoindole nuclei connected by nitrogen bridges in a 16-membered ring of alternating carbon and nitrogen atoms around a central metal atom (i.e., $C_{32}H_{16}N_8M$) which form stable chelates with metal cations. In these compounds, the ring center is occupied by a metal ion (such as a diamagnetic or a paramagnetic ion) that may, depending on the ion, carry one or two simple ligands. In addition, the ring periphery may be either unsubstituted or substituted.

Since E. Ben-Hur and I. Rosenthal disclosed the potential use of phthalocyanines as photosensitizers in 1985 (E. Ben-Hur and I. Rosenthal *Int. J. Radiat. Biol.* 47, 145-147, 1985), a great deal of research has followed producing a number of phthalocyanines for photodynamic therapy. Although prior studies with phthalocyanines have been generally disappointing, primarily because of the poor solubility characteristics of the basic ring, some of these compounds have attractive characteristics (C. M. Allen, W. M. Sharman, and J. E. van Lier, *J. Porphyrins Phthalocyanines* 5: 161-169, 2001; E. Ben-Hur and W.-S. Chan, Phthalocyanines in photobiology and their medical applications. In: *The Porphyrin Handbook* (K. M. Kadish, K. M. Smith, and R. Guilard, Eds.), vol. 19, *Applications of Phthalocyanines*, Elsevier Science, pp. 1-35 (2003)).

For example, unlike some of the porphyrin compounds, phthalocyanines strongly absorb clinically useful red light with absorption peaks falling between about 600 and 810 nm (Abernathy, Chad D., Anderson, Robert E., Kooistra, Kimberly L., and Laws, Edward R., *Neurosurgery, Vol.* 21, No. 4, pp. 468-473, 1987). Although porphyrins absorb light poorly in this wavelength region, as a result of the increased transparency of biological tissues at longer wavelengths, red light is normally used for photodynamic therapy. Thus, the greater absorption of red light by the phthalocyanines over porphyrins allows deeper potential penetration with the phthalocyanines in photodynamic treatment processes.

In addition, the phthalocyanines offer many benefits over the porphyrin components as photosensitizers in that the phthalocyanines are relatively easy to synthesize, purify, and characterize in contrast to the porphyrins, which are often difficult to prepare. Similarly, the metal phthalocyanines are exceptionally stable compounds in comparison to the porphyrin or porphyrin-like compounds. As a result, certain metallic phthalocyanines, such as aluminum phthalocyanine tetrasulfonate (AlPcS) and chloroaluminum phthalocyanine (AlPcCl), offer a number of advantages over porphyrins as therapeutic agents for photodynamic therapy.

Still, there remains a need for a convenient formulation of a photosensitizer that avoids potential toxicity to neighboring healthy tissue.

SUMMARY OF THE INVENTION

A series of compositions comprising aluminum and silicon phthalocyanines having relatively simple ligands carrying $NR_2$ or $NR_3^+$ functions were prepared and studied. Topical administration of compositions for photodynamic therapy offers the advantage of limiting therapy only to sites of involvement and prevents unwanted adverse effects especially the prolonged generalized skin photosensitivity such as that encountered in Photofrin® PDT.

One aspect of the invention relates to topical pharmaceutical compositions comprising a phthalocyanine, wherein a diamagnetic metal ion moiety is either coordinated or covalently bound to the phthalocyanine core. In certain embodiments, the present invention is directed to topical pharmaceutical compositions comprising a phthalocyanine compound, with modifying moieties linked to the central metal, which is selected from aluminum (Al), germanium (Ge), gallium (Ga), tin (Sn), and silicon (Si). Specifically, the present invention relates to aluminum, germanium, gallium, tin or silicon phthalocyanines having an axial group, or groups, carrying or terminating in an amine or ammonium function.

In an additional aspect, the present invention relates to methods of administering phthalocyanines. The phthalocyanines disclosed herein exhibit enhanced characteristics which make them well suited for topical application in photodynamic therapy when utilized alone or in combination with a pharmaceutical carrier.

In a further aspect, the present invention is directed to various methods for destroying cancer tissue, precancerous cells, photo-aged cells, damaged cells, or otherwise pathologic cells, or activated cells, such as lymphocytes or other cells of the immune system, or activated or inflamed tissue cells comprising topically administering to the cancer tissue or surrounding tissue an effective amount of a phthalocyanine composition having an axial group, or groups, carrying or terminating in an amine or ammonium function, and applying light of suitable wavelength and intensity to activate the composition thereby exerting a cell-killing, or cytotoxic, effect on the cancer tissue, precancerous cells, photo-aged cells, damaged cells, or otherwise pathologic cells, or activated cells, such as lymphocytes or other cells of the immune system, or activated or inflamed tissue cells.

Another aspect of the invention relates to a method for treating epithelial cancer, comprising administering a photosensitizer to an epithelial surface and irradiating the epithelial surface.

Another aspect of the invention relates to methods of preparing topical phthalocyanine compositions (or compounds) suitable for use as photosensitizers in photodynamic therapy. Specifically, the invention relates to metal-coordinated phthalocyanines having substituted amine or ammonium axial ligands attached to a central metal, and the use of these phthalocyanine compositions for the treatment of cancer or other epithelial cell abnormalities through photosensitization.

BRIEF DESCRIPTION OF THE DRAWINGS

The following is a brief description of the drawings which are presented for the purpose of illustrating the invention and not for the purpose of limiting them.

DETAILED DESCRIPTION OF THE INVENTION

Figure 1:
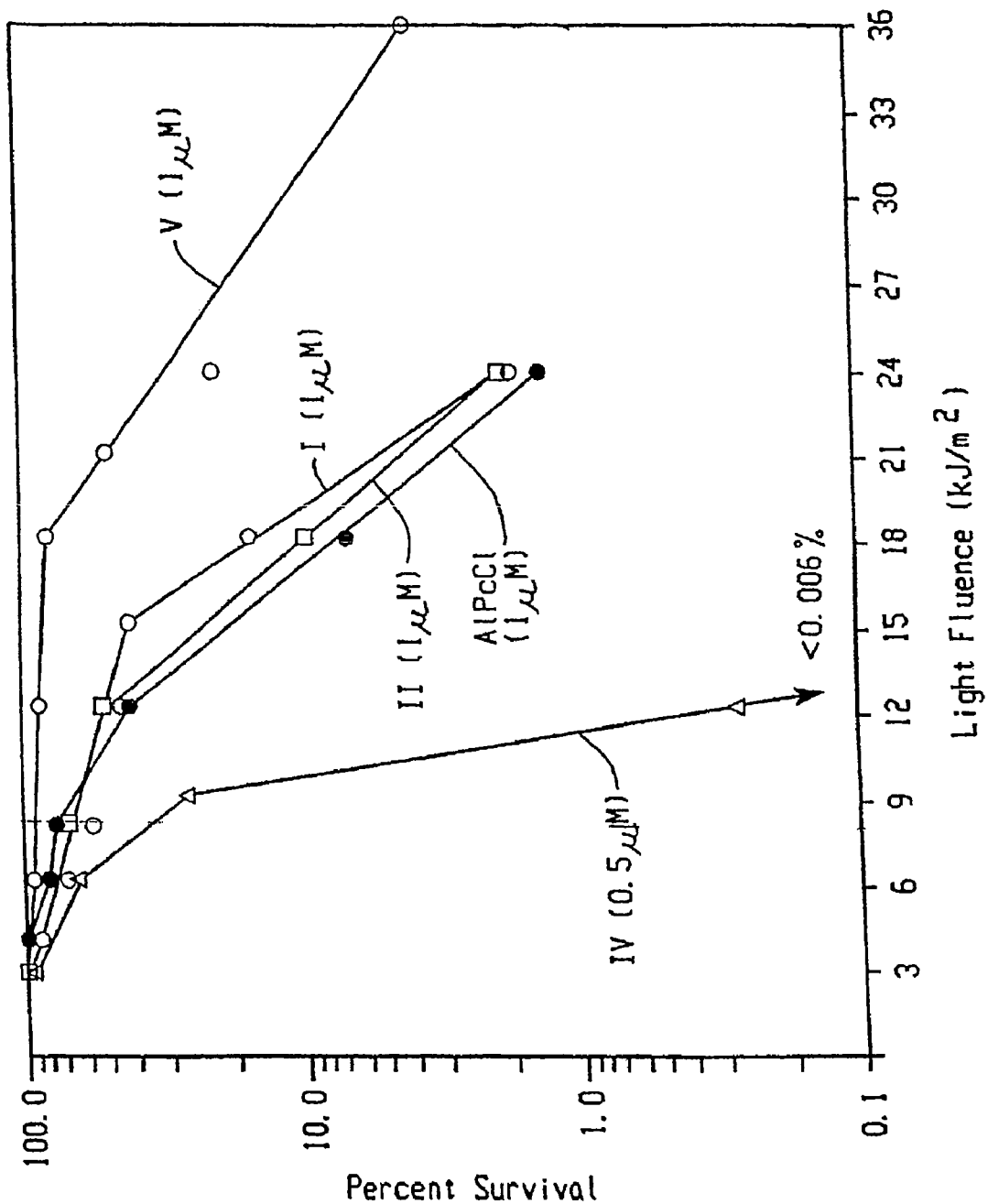
FIG. 1 is a graph illustrating the photodynamic efficacy of the various compositions of the present invention in comparison to AlPcCl. The phthalocyanine composition compounds of the present invention were tested for their photodynamic efficiency against Chinese hamster fibroblast V79 cells by colony formation. Monolayer cultures were treated with the indicated phthalocyanine composition for 18 hours, irradiated with various fluences of red light, and immediately trypsinized and replated at appropriate aliquots in triplicate. Colonies of at least 50 cells were counted after 7-10 days. The plating efficiency of the untreated cells was approximately 90%.

The present invention relates in part to methods of preparing phthalocyanine compounds and topical compositions suitable for use in photodynamic therapy. Specifically, the invention relates to Al, Ga, Si, Ge, and/or Sn phthalocyanines having substituted amine or quaternary ammonium axial ligands attached to the central metal, and the use of these phthalocyanine compositions for the treatment of cancer through photosensitization.

Although research has recently been directed to the use of various phthalocyanines for photodynamic therapy, this activity has been principally directed to phthalocyanines with peripheral substituents, and little, if any, attention has been given to phthalocyanines with complex metal ligands. The limited variety of phthalocyanines which have been tested vary greatly in their photosensitizing activity. Metal-free phthalocyanines show poor photodynamic activity (Abernathy, C. D., R. E. Anderson, K. L. Kooistra, E. R. Laws, Jr., Neurosurgery, 1987, 21, 468-473; Chan, W. S., J. F. Marshall, G. Y. F. Lam, I. R. Hart, Cancer Res. 1988, 48, 3040-3044;

Sonoda, M., C. M. Krishna, P. Riesz, Photochem Photobiol. 1987, 46, 625-632) as do phthalocyanines containing paramagnetic metals. In contrast, phthalocyanines containing diamagnetic metals have been shown to demonstrate improved activity, which is thought to be a due to the long half-life of the triplet state.

In the compounds and compositions of the present invention, axial ligands carrying or terminating in an amine function or a quaternary ammonium function are attached to the central metal. As a result, it is believed that these more complex axial ligands give the new phthalocyanine compositions the potential to bind to the various species that assist in transporting the composition to and from their targets, as well as enhance the potential for the phthalocyanines to bind to their specific target cells.

Some of the phthalocyanines having substituted amine or ammonium axial ligands attached to either aluminum or silicon as the central metal are much more effective in producing photodynamic activity when compared with chloroaluminum phthalocyanine (AlPcCl). The enhanced cytotoxic effects produced are presumably due to the increased cellular uptake of the compositions and/or the increased loss of clonogenicity as a function both of the concentration of the phthalocyanine and the red light fluence.

Certain phthalocyanine compounds of the invention generally have a structure of the following formula (I) or a pharmaceutically acceptable salt thereof:

[Pc.M]     (I)

wherein Pc is a substituted or unsubstituted phthalocyanine; and

M is a diamagnetic metal ion, optionally complexed with or covalently bound to one or two axial ligands, wherein the metal ion is coordinated to the phthalocyanine moiety.

In certain embodiments, the axial ligand(s) is (or are independently) selected from H, alkylamino, alkylthio, alkoxy, alkylseleno, alkylsulfonyl, $C(S)NHC_6H_{11}O_5$, $(CH_2)_nN((CH)_o(CH_3))_2$, $OC(O)CH_3$, $OC(O)$, $CS$, $CO$, $CSe$, $OH$, and an alkyl group having from 1 to 12 carbon atoms.

Another aspect of the invention relates to phthalocyanine compositions including a compound generally characterized by the following formula (II) or a pharmaceutically acceptable salt thereof

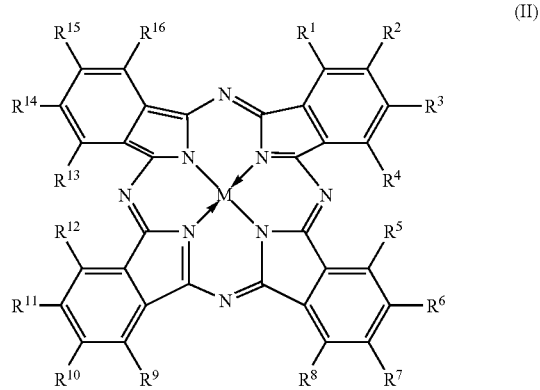

(II)

wherein M is a diamagnetic metal ion optionally complexed with or covalently bound to one or two axial ligands, wherein the metal ion is coordinated to the phthalocyanine moiety; and $R^1$-$R^{16}$ are each independently selected from hydrogen, halogen, nitro, cyano, hydroxy, thiol, amino, carboxy, aryl, heteroaryl, carbocyclyl, heterocyclyl, $C_{1-20}$alkyl, $C_{1-20}$alkenyl, $C_{1-20}$alkynyl, $C_{1-20}$alkoxy, $C_{1-20}$acyl, $C_{1-20}$alkylcarbonyloxy, $C_{1-20}$aralkyl, $C_{1-20}$hetaralkyl, $C_{1-20}$-carbocyclylalkyl, $C_{1-20}$heterocyclylalkyl, $C_{1-20}$aminoalkyl, $C_{1-20}$alkylamino, $C_{1-20}$thioalkyl, $C_{1-20}$alkylthio, $C_{1-20}$hydroxyalkyl, $C_{1-20}$alkyloxycarbonyl, $C_{1-20}$alkylaminocarbonyl, $C_{1-20}$alkylcarbonylamino, $C_{1-10}$alkyl-Z-$C_{1-10}$alkyl;

$R^{17}$ is selected from hydrogen, $C_{1-20}$acyl, $C_{1-20}$alkyl, and $C_{1-20}$aralkyl; and Z is selected from S, $NR^{17}$, and O.

In certain embodiments, the axial ligand(s) is (or are independently) selected from H, alkylamino, alkylthio, alkoxy, alkylseleno, alkylsulfonyl, $C(S)NHC_6H_{11}O_5$, $(CH_2)_nN((CH)_o(CH_3))_2$, $OC(O)CH_3$, $OC(O)$, $CS$, $CO$, $CSe$, $OH$, and an alkyl group having from 1 to 12 carbon atoms.

Another aspect of the invention relates to phthalocyanine compositions including a compound generally characterized by the following formula (III) or a pharmaceutically acceptable salt thereof

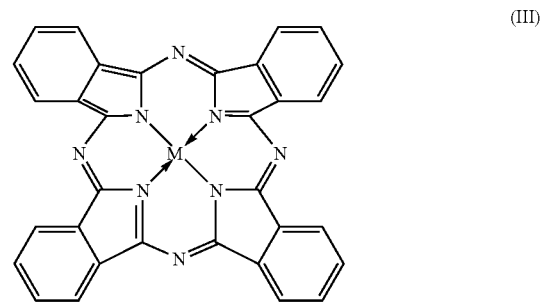

(III)

wherein M is $(G)_aY[(OSi(CH_3)_2(CH_2)_bN_c(R')_d(R'')_e)_fX_g]_p$;

Y is selected from Si, Al, Ga, Ge, or Sn;

R' is selected from H, $CH_3$, $C_2H_5$, $C_4H_9$, $C_4H_8NH$, $C_4H_8N$, $C_4H_8NCH_3$, $C_4H_8S$, $C_4H_8O$, $C_4H_8Se$, $OC(O)CH_3$, $OC(O)$, $CS$, $CO$, $CSe$, $OH$, $C_4H_8N(CH_2)_3CH_3$, $(CH_2)_2N(CH_3)_2$, $(CH_2)_nN((CH_2)_o(CH_3))_2$, and an alkyl group having from 1 to 12 carbon atoms;

R'' is selected from H, $SO_2CH_3$, $(CH_2)_2N(CH_3)_2$, $(CH_2)_{11}CH_3$, $C(S)NHC_6H_{11}O_5$, $(CH_2)_nN((CH_2)_o(CH_3))_2$, and an alkyl group having from 1 to 12 carbon atoms;

G is selected from OH and $CH_3$;

X is selected from I, F, Cl, or Br;

a is 0 or 1;

b is an integer from 2 to 12;

c is 0 or 1;

d is an integer from 0 to 3;

e is an integer from 0 to 2;

f is 1 or 2;

g is 0 or 1;

n is an integer from 1 to 12;

o is an integer from 1 to 11; and p is 1 or 2.

In certain embodiments, M is $AlOSi(CH_3)_2(CH_2)_3N(CH_3)_2$; $AlOSi(CH_3)_2(CH_2)_3N(CH_3)_3{}^+I^-$; $CH_3SiOSi(CH_3)_2(CH_2)_3N(CH_3)_2$; $HOSiOSi(CH_3)_2(CH_2)_3N(CH_3)_2$; $HOSiOSi(CH_3)_2(CH_2)_3N(CH_3)_3{}^+I^-$; $Si[OSi(CH_3)_2(CH_2)_3N(CH_3)_3{}^+I^-]_2$; $Si[OSi(CH_3)_2(CH_2)_4NH_2]_2$; $Si[OSi(CH_3)_2(CH_2)_4NHSO_2CH_3]_2$; $HOSiOSi(CH_3)_2(CH_2)_4NHSO_2CH_3$; $HOSiOSi(CH_3)_2(CH_2)_3N(CH_2CH_3)(CH_2)_2N(CH_3)_2$; $Si[OSi(CH_3)_2(CH_2)_4 NHCSNHC_6H_{11}O_5]_2$; $Si[OSi(CH_3)_2(CH_2)_3N(CH_3)_2]_2$; $HOSiOSi(CH_3)_2(CH_2)_3OCOCH_3$; $HOSiOSi(CH_3)_2(CH_2)_3OH$; $Si[OSi(CH_3)_2(CH_2)_3N(CH_2CH_3)(CH_2)_2N(CH_3)_2]_2$; $HOSiOSi(CH_3)_2(CH_2)_3NC_4H_8O$; AlOSi (CH$_3$)$_2$(CH$_2$)$_3$N$^+$(CH$_3$)$_2$(CH$_2$)$_{11}$CH$_3$I$^-$; HOSiOSi(CH$_3$)$_2$(CH$_2$)$_8$N(CH$_3$)$_2$; Si[OSi(CH$_3$)$_2$(CH$_2$)$_3$NC$_4$H$_8$O]$_2$; HOSiOSi(CH$_3$)$_2$(CH$_2$)$_3$NC$_4$H$_8$S; HOSiOSi(CH$_3$)$_2$(CH$_2$)$_3$N(CH$_2$)$_3$(CH$_3$)$_2$; HOSiOSi(CH$_3$)$_2$(CH$_2$)$_3$NCS; HOSiOSi(CH$_3$)$_2$(CH$_2$)$_3$N[(CH$_2$)$_3$N(CH$_3$)$_2$]$_2$; HOSiOSi(CH$_3$)$_2$(CH$_2$)$_3$NC$_4$H$_8$NCH$_3$; Si[OSi(CH$_3$)$_2$(CH$_2$)$_3$NC$_4$H$_8$NCH$_3$]$_2$; HOSiOSi(CH$_3$)$_2$(CH$_2$)$_3$NC$_4$H$_8$N(CH$_2$)$_3$CH$_3$; or Si[OSi(CH$_3$)$_2$(CH$_2$)$_3$NC$_4$H$_8$NH]$_2$.

In preferred embodiments, M is represented by HOSiOSi(CH$_3$)$_2$(CH$_2$)$_3$N(CH$_3$)$_2$; HOSiOSi(CH$_3$)$_2$(CH$_2$)$_3$N(CH$_2$CH$_3$)(CH$_2$)$_2$N(CH$_3$)$_2$; HOSiOSi(CH$_3$)$_2$(CH$_2$)$_3$NC$_4$H$_8$O; HOSiOSi(CH$_3$)$_2$(CH$_2$)$_8$N(CH$_3$)$_2$ or a pharmaceutically acceptable salt thereof. In the most preferred embodiment, M is represented by HOSiOSi(CH$_3$)$_2$(CH$_2$)$_3$N(CH$_3$)$_2$ or a pharmaceutically acceptable salt thereof.

Another aspect of the invention relates to phthalocyanine compounds and compositions including a compound generally characterized by the following formula (IV) or a pharmaceutically acceptable salt thereof

$$\text{SiPc}[(OR^1)(OR^2)] \qquad (IV)$$

wherein R$^1$ is selected from H and R$^2$;
each R$^2$ is independently Si(R$^3$)$_2$(C$_{1-12}$alkyl-N(C$_{1-12}$alkyl)$_2$);
each R$^3$ is independently selected from C$_{1-12}$alkyl, C$_{1-12}$alkoxy, C$_{1-12}$aralkyl, aryloxy, and aryl.

The phthalocyanine ligand, Pc, may be substituted or unsubstituted.

In certain embodiments, the phthalocyanine compositions comprise HOSiPcOSi(CH$_3$)$_2$(CH$_2$)$_3$N(CH$_3$)$_2$ (PcIV) or SiPc[OSi(CH$_3$)$_2$(CH$_2$)$_3$N(CH$_3$)$_2$]$_2$ (PcXII).

Pharmaceutically acceptable salt refers to the relatively non-toxic, inorganic and organic acid addition salts of the photosensitizer(s). These salts can be prepared in situ during the final isolation and purification of the photosensitizer(s), or by separately reacting a purified photosensitizer(s) in its free base form with a suitable organic or inorganic acid, and isolating the salt thus formed. Representative salts include the hydrobromide, hydrochloride, sulfate, bisulfate, phosphate, nitrate, acetate, pyruvate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts, and the like. (See, for example, Berge et al. (1977) "Pharmaceutical Salts", *J. Pharm. Sci.* 66:1-19). Preferred pharmaceutically acceptable salts are the hydrochloric and pyruvate salts. The most preferred pharmaceutically acceptable salt is the pyruvate.

Another aspect of the invention relates to a composition comprising a compound of any one of formulae I-IV, or a pharmaceutically acceptable salt thereof, and a pharmaceutically acceptable carrier. In certain embodiments, the composition is applied to an epithelial, mesothelial, synovial, fascial, or serosal surface, including, but not limited to, the eye, esophagus, mucous membrane, bladder, joint, tendon, ligament, bursa, gastrointestinal, genitourinary, pleural, pericardial, pulmonary, or uroepithelial surfaces. In certain embodiments, the composition is applied to the surface of the skin.

Another aspect of the invention relates to a method for treating epithelial cancer, comprising administering a photosensitizer to an epithelial surface and irradiating the epithelial surface. In certain embodiments, the method further comprises a pharmaceutically acceptable carrier. In certain preferred such embodiments, the photosensitizer is a phthalocyanine or a pharmaceutically acceptable salt thereof. In certain preferred such embodiments, the phthalocyanine is a compound of any one of formulae I-IV or a pharmaceutically acceptable salt thereof. Epithelial cancers include, but are not limited to basal cell carcinoma, squamous cell carcinoma, carcinosarcoma, adenocystic carcinoma, epidermoid carcinoma, nasopharyngeal carcinoma, and renal cell carcinoma.

In certain embodiments, the invention relates to a method for treating skin cancer, comprising administering a photosensitizer to an area of skin and irradiating the skin. In certain embodiments, the method further comprises a pharmaceutically acceptable carrier. In certain preferred such embodiments, the photosensitizer is a phthalocyanine or a pharmaceutically acceptable salt thereof. In certain preferred such embodiments, the phthalocyanine is a compound of any one of formulae I-IV or a pharmaceutically acceptable salt thereof.

Another aspect of the invention relates to a diagnostic assay for cancerous tissue, precancerous, or otherwise damaged or aged, comprising administering a compound of any one of formulae I-IV, or a pharmaceutically acceptable salt thereof, and detecting the amount of Pc in the cells, wherein cancerous or otherwise pathologic tissue has a significantly higher amount of retained Pc as compared to a normal cell. In certain such embodiments, the compound is administered topically.

Topical administration of phthalocyanine(s) or a pharmaceutically acceptable salt thereof may be accomplished using, powders, sprays, ointments, pastes, creams, lotions, gels, solutions, or patches. The active component may be mixed under sterile conditions with a pharmaceutically acceptable carrier, and with any preservatives, buffers, or propellants which may be required. The ointments, pastes, creams, solutions, foams, lacquers, oils and gels may contain excipients in addition to phthalocyanine(s). These formulations may contain a phthalocyanine within or on micro or nanoparticles, liposomes, beads, polymer matrices, sponges, osmotic pumps, or other structures.

Powders and sprays can contain, in addition to a phthalocyanine, excipients such as lactose, talc, silicic acid, aluminum hydroxide, calcium silicates, and polyamide powder, or mixtures of these substances. Sprays can additionally contain customary propellants, such as chlorofluorohydrocarbons and volatile unsubstituted hydrocarbons, such as butane and propane. In certain embodiments, a composition comprising a compound of any one of formulae I-IV may be prepared according to U.S. Pat. Nos. 6,617,356, 5,914,334, or 6,617,356, the disclosures of which are incorporated herein in their entirety.

The phthalocyanine can be alternatively administered by aerosol. This is accomplished by preparing an aqueous aerosol, liposomal preparation, or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars, or sugar alcohols. Aerosols generally are prepared from isotonic solutions.

Transdermal patches have the added advantage of providing controlled delivery of a phthalocyanine to the body. Such dosage forms can be made by dissolving or dispersing the agent in the proper medium. Absorption enhancers can also be used to increase the flux of the photosensitizer(s) into the skin. The rate of such flux can be controlled by either providing a rate controlling membrane or dispersing the peptidomimetic in a polymer matrix or gel.

Delivery of phthalocyanines across an epithelial, epidermal, serosal or mucosal surface may be accomplished using application of an electrical current and a charged solvent solution, such as iontophoresis.

"Pharmaceutically acceptable carrier" as used herein means a pharmaceutically acceptable material, composition or vehicle, such as a liquid or solid filler, diluent, excipient, solvent or encapsulating material, involved in carrying or transporting the subject chemical from one organ or portion of the body, to another organ or portion of the body. Each carrier must be "acceptable" in the sense of being compatible with the other ingredients of the formulation and not injurious to the patient. Some examples of materials which can serve as pharmaceutically acceptable carriers include: (1) sugars, such as lactose, glucose, and sucrose; (2) starches, such as corn starch and potato starch; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The specific process utilized to synthesize the aluminum and silicon phthalocyanine compounds of the present invention, and the enhanced results produced through the use of these new compounds for photodynamic therapy, are more particularly described below in the following examples.

Definitions

The term "$C_{x-y}$acyl" refers to a group represented by the general formula:

$$C_{x-y}\text{alkyl-C(O)}\text{—}$$

The term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-tirfluoroethyl, etc. $C_0$ alkyl indicates a hydrogen where the group is in a terminal position, a bond if internal. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond respectively.

The term "alkoxy" refers to an alkyl group having an oxygen attached thereto. Representative alkoxy groups include methoxy, ethoxy, propoxy, tert-butoxy and the like. An "ether" is two hydrocarbons covalently linked by an oxygen. Accordingly, the substituent of an alkyl that renders that alkyl an ether is or resembles an alkoxy.

The term "$C_{x-y}$aralkyl", as used herein, refers to a $C_{x-y}$alkyl group substituted with an aryl group.

The terms "amine" and "amino" are art-recognized and refer to both unsubstituted and substituted amines and salts thereof, e.g., a moiety that can be represented by the general formulae:

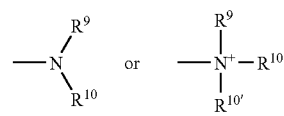

wherein $R^9$, $R^{10}$ and $R^{10'}$ each independently represent a hydrogen, an alkyl, an alkenyl, —$(CH_2)_m$—$R^8$ or $R^9$ and $R^{10}$ taken together with the N atom to which they are attached complete a heterocycle having from 4 to 8 atoms in the ring structure; $R^8$ represents an aryl, a cycloalkyl, a cycloalkenyl, a heterocyclyl or a polycyclyl; and m is zero or an integer from 1 to 8. In preferred embodiments, only one of $R^9$ or $R^{10}$ can be a carbonyl, e.g., $R^9$, $R^{10}$, and the nitrogen together do not form an imide. In even more preferred embodiments, $R^9$ and $R^{10}$ (and optionally $R^{10'}$) each independently represent a hydrogen, an alkyl, an alkenyl, or —$(CH_2)_m$—$R^8$.

The term "aryl" as used herein includes 5-, 6-, and 7-membered substituted or unsubstituted single-ring aromatic groups in which each atom of the ring is carbon. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The terms "carbocycle" and "carbocyclyl", as used herein, refer to a non-aromatic substituted or unsubstituted ring in which each atom of the ring is carbon. The terms "carbocycle" and "carbocyclyl" also include polycyclic ring systems having two or more cyclic rings in which two or more carbons are common to two adjoining rings wherein at least one of the rings is carbocyclic, e.g., the other cyclic rings can be cycloalkyls, cycloalkenyls, cycloalkynyls, aryls, heteroaryls, and/or heterocyclyls.

The term "carbonyl" is art-recognized and includes such moieties as can be represented by the general formula:

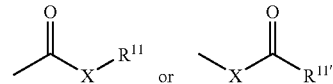

wherein X is a bond or represents an oxygen or a sulfur, and $R^{11}$ represents a hydrogen, an alkyl, an alkenyl, —$(CH_2)_m$—$R^8$ or a pharmaceutically acceptable salt, $R^{11'}$ represents a hydrogen, an alkyl, an alkenyl or —$(CH_2)_m$—$R^8$, where m and $R^8$ are as defined above. Where X is an oxygen and $R^{11}$ or $R^{11'}$ is not hydrogen, the formula represents an "ester". Where X is an oxygen, and $R^{11}$ is a hydrogen, the formula represents a "carboxylic acid".

The term "$C_{x-y}$heteroaralkyl", as used herein, refers to a $C_{x-y}$alkyl group substituted with a heteroaryl group.

The terms "heteroaryl" includes substituted or unsubstituted aromatic 5- to 7-membered ring structures, more preferably 5- to 6-membered rings, whose ring structures include one to four heteroatoms. The term "heteroaryl" also includes polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, triazole, pyrazole, pyridine, pyrazine, pyridazine and pyrimidine, and the like.

The term "heteroatom" as used herein means an atom of any element other than carbon or hydrogen. Preferred heteroatoms are nitrogen, oxygen, phosphorus, and sulfur.

The terms "heterocyclyl" or "heterocyclic group" refer to substituted or unsubstituted non-aromatic 3- to 10-membered ring structures, more preferably 3- to 7-membered rings, whose ring structures include one to four heteroatoms. The term terms "heterocyclyl" or "heterocyclic group" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The terms "PcIV" and "Pc 4", as used herein represent a compound having a structure of Formula (III), wherein M is $HOSiPcOSi(CH_3)_2(CH_2)_3N(CH_3)_2$.

The terms "polycyclyl" or "polycyclic" refer to two or more rings (e.g., cycloalkyls, cycloalkenyls, cycloalkynyls, aryls, heteroaryls, and/or heterocyclyls) in which two or more carbons are common to two adjoining rings, e.g., the rings are "fused rings". Each of the rings of the polycycle can be substituted or unsubstituted.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

A "therapeutically effective amount" of a compound with respect to the subject method of treatment, refers to an amount of the compound(s) in a preparation which, when administered as part of a desired dosage regimen (to a mammal, preferably a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

As used herein, the term "treating" or "treatment" includes reversing, reducing, or arresting the symptoms, clinical signs, and underlying pathology of a condition in manner to improve or stabilize a subject's condition.

EXAMPLES

Synthesis of Phthalocyanines $CH_3OSi(CH_3)_2(CH_2)_3N(CH_3)_2$—Under argon gas a solution of $CH_3MgCl$ in tetrahydrofuran (3.0 M, 45 mL) was added dropwise to a cool (ice bath) solution of $(CH_3O)_3Si(CH_2)_3N(CH_3)_2$ (11 mL) in tetrahydrofuran (100 mL), and the resulting suspension was stirred for 2 hours while being kept cool (at about 5° C.). Methanol (20 mL) was then added to the suspension and the resulting mixture was filtered, the solid was washed with ether (50 mL) and the washings and filtrate were combined and concentrated on a rotary evaporator (45° C.). The concentrate was fractionally distilled under vacuum (45 torr) and a selected fraction (86-88° C.) was retained (5.0 g, 55%): NMR (CDCl$_3$) δ 3.42 (s, 3 H), 2.24 (m, 2 H), 2.20 (s, 3 H), 1.49 (m, 2 H), 0.57 (m, 2 H), 0.10 (s, 3 H). The compound is a colorless liquid.

$AlPcOSi(CH_3)_2(CH_2)_3N(CH_3)_2$—Compound I. A mixture of $CH_3OSi(CH_3)_2(CH_2)_3N(CH_3)_2$ (203 mg) produced above and a suspension of AlPcOH xH$_2$O (56 mg) and 2-ethylpyridine (15 mL) that had been dried by distillation (3 mL of distillate) was refluxed for 45 minutes and filtered. The filtrate was evaporated to dryness on a rotary evaporator (about 40° C.) and the solid was dissolved $CH_2Cl_2$ (2 mL). Hexanes (3 mL) were added to the solution and the resulting suspension was filtered. The solid was washed (benzene and hexanes), vacuum dried (65° C.), and weighed (63 mg, 98% assuming AlPcOH.3H$_2$O); NMR (C$_5$D$_5$N, 70° C.) δ 9.65 (m, 1,4-PcH), 8.28 (m, 2,3-PcH), 1.63 (s, 3 H), 0.99 (m, 2 H), −0.50 (m, 2 H), −1.80 (m, 2 H), −2.33 (s, 3 H).

The compound is blue and is soluble in $CH_2Cl_2$ and toluene.

$AlPcOSi(CH_3)_2(CH_2)_3N(CH_3)_3^+I^-$—Compound II. A mixture of $AlPcOSi(CH_3)_2(CH_2)_3N(CH_3)_2$ (30 mg), benzene (10 mL), and $CH_3I$ (15 μL) was refluxed for 1.5 hours, cooled, and filtered. The solid was vacuum dried (60° C.) and weighed (31 mg, 86%): NMR(C$_5$D$_5$N, 70° C.) δ 9.75 (m, 1,4-PcH), 8.34 (m, 2,3-PcH), 2.90 (s, 3 H), 2.02 (m, 2 H), −0.53 (m, 2 H), −1.87 (m, 2 H), −2.40 (s, 3 H).

The compound is a blue solid and is soluble in $CH_2Cl_2$ and $CH_3OH$ but is insoluble in toluene and $H_2O$.

$CH_3SiPcOSi(CH_3)_2(CH_2)_3N(CH_3)_2$—Compound III. Procedures in this synthesis that were carried out under low light conditions (room lights off, shades drawn) are identified by the symbol 1. A mixture of $CH_3OSi(CH_3)_2(CH_2)_3N(CH_3)_2$ (224 mg) and a suspension of $CH_3SiPcOH$ (117 mg) and pyridine (25 mL) that had been dried by distillation (1) was slowly distilled (1) for 3 h (10 mL of distillate) and then filtered (1, no solid). The filtrate was evaporated to dryness on a rotary evaporator (1, 75° C.), and the solid was dissolved in $CH_2Cl_2$ (12 mL). Hexanes (30 mL) were added to the solution (1) and the resulting suspension was filtered (1). The solid was washed (hexanes), vacuum dried (65° C.), and weighed (11 mg, 76%): mp>260° C.; NMR (CDCl$_3$) δ 9.63 (m, 1,4-PcH), 8.33 (m, 2,3-PcH), 1.74 (s, 3 H), 1.01 (m, 2 H, −1.18 (m, 2 H), −2.25 (m, 2 H), −2.96 (s, 6 H), −6.35 (s, 3 H).

The compound is dark green and is soluble in $CH_2Cl_2$ and toluene. Solutions of it are rapidly photolyzed by white light.

$HOSiPcOSi(CH_3)_2(CH_2)_3N(CH_3)_2$—Compound IV. A mixture of $CH_3SiPcOSi(CH_3)_2(CH_2)_3N(CH_3)_2$ (35 mg), $N(C_2H_5)_3$ saturated with $H_2O$ (0.2 mL), and toluene (70 mL) was irradiated with an incandescent light (300 W in 35 mm slide projector) for 15 minutes. The resulting suspension was concentrated on a rotary evaporator (~45° C.) and the concentrate (~5 mL) was diluted with hexanes (1 mL). The suspension formed was filtered and the solid was washed (hexanes), vacuum dried (65° C.), and weighed (33 mg, 96%): mp>260° C.; NMR (dimethylformamide-d$_7$, 70° C.) δ 9.68 (m, 1,4-PcH), 8.47 (m, 2,3-PcH), 1.52 (s, 3 H), 0.74 (m, 2 H), −1.11 (m, 2 H), −2.27 (m, 2 H), −2.89 (s, 3 H). MS-HRFAB exact mass m/z calculated for C$_{39}$H$_{35}$N$_9$O$_2$Si$_2$M+7.17.2452. Found 717.2422.

The compound is blue and is soluble in CH$_2$Cl$_2$ and toluene.

HOSiPcOSi(CH$_3$)$_2$(CH$_2$)$_3$N(CH$_3$)$_3$$^+$I$^-$—Compound V. A mixture of HOSiPcOSi(CH$_3$)$_2$(CH$_2$)$_3$N(CH$_3$)$_2$ (24 mg), CH$_3$I (25 μL), and benzene (10 mL) was refluxed for 1.5 hours, cooled, and filtered. The solid was washed (benzene), vacuum dried (65° C.), and weighed (23 mg, 81%): NMR (dimethylformamide-d$_7$, 70° C.) δ9.66 (m, 1,4-PcH), 8.45 (m, 2,3-PcH), 2.87 (s, NCH$_3$), 2.06 (m, γ-CH$_2$), −0.97 (m, β—CH$_2$), −2.25 (m, α-CH$_2$), −2.83 (s, SiCH$_3$). MS-HRFAB exact mass m/z calculated for C$_{40}$H$_{38}$N$_9$O$_2$Si$_2$ (M-I)$^+$ 732.2687. Found 732.2668.

The compound is blue. It is soluble in CH$_2$Cl$_2$ and CH$_3$OH but is insoluble in toluene and H$_2$O.

SiPc[OSi(CH$_3$)$_2$(CH$_2$)$_3$N(CH$_3$)$_2$]$_2$. A mixture of CH$_3$OSi (CH$_3$)$_2$(CH$_2$)$_3$N(CH$_3$)$_2$ (239 mg) and a suspension of SiPc (OH)$_2$ (232 mg) and 2-ethylpyridine (30 mL) that had been dried by distillation (~2 mL of distillate) was slowly distilled for 2 hours (~5 mL of distillate). The resulting solution was filtered, the filtrate was evaporated to dryness on a rotary evaporator (~60° C.), and the solid was dissolved in CH$_2$Cl$_2$ (3.5 mL). The CH$_2$Cl$_2$ solution was diluted with hexanes (~40 mL), the suspension formed was filtered, and the solid was washed (hexanes), air dried, and weighed (263 mg, 76%); NMR (CDCl$_3$), δ 9.63 (m, 1,4-PcH), 8.34 (m, 2,3-PcH), 1.65 (s, NCH$_3$), 0.90 (m, γ-CH$_2$), −1.10 (m, β-CH$_2$), −2.26 (m, α-CH$_2$), −2.87 (s, SiCH$_3$).

The compound is blue and is soluble in CH$_2$Cl$_2$ and toluene.

SiPc[OSi(CH$_3$)$_2$(CH$_2$)$_3$N(CH$_3$)$_3$)$^+$I$^-$]$_2$—Compound VI. A mixture of SiPc[OSi(CH$_3$)$_2$(CH$_2$)$_3$N(CH$_3$)$_2$]$_2$ produced above (30 mg), CH$_3$I (36 μL) and benzene (5 mL) was refluxed for 1.5 hours, cooled, and filtered. The solid was washed (benzene, hexanes), vacuum dried (60° C.), and weighed (32 mg, 79%): NMR (CD$_3$OD) δ 9.63 (m, 1,4-PcH), 8.41 (m, 2,3-PcH), 1.65 (s, NCH$_3$), 0.90 (m, γ-CH$_2$), −1.10 (m, β-CH$_2$), −2.21 (m, α-CH$_2$), −2.90 (s, SiCH$_3$).

The compound is blue and is soluble in CH$_2$Cl$_2$ and CH$_3$OH but is insoluble in toluene. It disperses in H$_2$O but doses not dissolve in it.

Additional Phthalocyanine Compounds

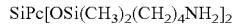  Compound VII

A mixture of CH$_3$OSi(CH$_3$)$_2$(CH$_2$)$_4$NH$_2$ (100 μL, 0.53 mmol), SiPc(OH)$_2$ (65 mg, 0.11 mmol) and pyridine (15 mL) was distilled for 30 minutes (~5 mL distillate) and filtered. The filtrate was evaporated to dryness with a rotary evaporator (~70° C.). The solid was dissolved in ethanol (4 mL), precipitated from the solution with water (3 mL), recovered by filtration, washed (ethanol-water solution, 2:1), vacuum dried (~60° C.) and weighed (81 mg, 0.097 mmol, 88%): UV-Vis (toluene) λ$_{max}$ 669 nm; NMR (CDCl$_3$) δ 9.67 (m, 1,4-PcH), 8.36 (m, 2,3-PcH), 1.71 (t, δ-CH$_2$), 0.10 (m, γ-CH$_2$), −1.33 (m, β-CH$_2$), −2.20 (m, α-CH$_2$), −2.87 (s, SiCH$_3$). MS-HRFAB exact mass, m/z: calculated for C$_{44}$H$_{48}$N$_{10}$O$_2$Si$_3$ (M)$^+$, 832.3270; found, 832.3261, 832.3274. The compound is blue and is soluble in CH$_2$Cl$_2$, dimethylformamide, pyridine and ethanol.

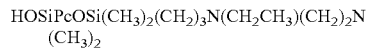  Compound X

To prepare CH$_3$OSi(CH$_3$)$_2$(CH$_2$)$_3$N(CH$_2$CH$_3$)(CH$_2$)$_2$N (CH$_3$)$_2$, a solution of CH$_3$OSi(CH$_3$)$_2$(CH$_2$)$_3$Cl (5.06 g, 30 mmol), CH$_3$CH$_2$NH(CH$_2$)$_2$N(CH$_3$)$_2$ (5.0 mL, 61 mmol) and CH$_3$OH (5.0 mL) was refluxed for 6 hours and then distilled under gradually reduced pressure (20 torr final). The remainder was diluted with ether (20 mL) and filtered. The solid was washed (ether) and the washings and the filtrate were combined and concentrated with a rotary evaporator (~25° C.). The concentrate was fractionally distilled under vacuum (7 mtorr) and a selected fraction (30-35° C.) was retained (432 mg, 1.8 mmol, 6%): NMR (CDCl$_3$) δ 3.40 (s, CH$_3$O), 2.53 (m, NCH$_2$CH$_3$ and CH$_2$CH$_2$ NCH$_3$), 2.37 (m, γ-CH$_2$ and CH$_2$CH$_2$NCH$_3$), 2.21 (s, NCH$_3$), 1.46 (m, β-CH$_2$), 0.97 (t, NCH$_2$CH$_3$), 0.52 (m, α-CH$_2$), 0.07 (s, SiCH$_3$). The compound is a colorless oil.

All steps but the finally drying step of this procedure were carried out under low-intensity illumination. To prepare CH$_3$SiPcOSi(CH$_3$)$_2$(CH$_2$)$_3$N(CH$_2$CH$_3$)(CH$_2$)$_2$N(CH$_3$)$_2$, a mixture of the CH$_3$OSi(CH$_3$)$_2$(CH$_2$)$_3$N(CH$_2$CH$_3$)(CH$_2$)$_2$N (CH$_3$)$_2$ (432 mg, 1.8 mmol) and a suspension of CH$_3$SiPcOH (291 mg, 0.51 mmol) and pyridine (120 mL) that had been dried by distillation (~23 mL of distillate) was slowly distilled for 3 hours (~5 mL of distillate) and then filtered. The filtrate was evaporated to dryness with a rotary evaporator (~80° C.). The solid was dissolved in CH$_2$Cl$_2$ (1 mL), precipitated from the solution with hexanes (20 mL), recovered by filtration, washed (CH$_3$OH and hexanes), vacuum dried (~90° C.) and weighed (306 mg, 0.39 mmol, 76%): NMR (CD$_2$Cl$_2$) δ 69.68 (m, 1,4-Pc H), 8.40 (m, 2,3-Pc H), 2.01 (s, NCH$_3$), 1.85 (s, NCH$_2$CH$_2$N), 1.83 (q, NCH$_2$CH$_3$), 0.98 (m, γ-CH$_2$), 0.61 (t, NCH$_2$CH$_3$), −1.18 (m, β-CH$_2$), −2.39 (m, α-CH$_2$), −2.94 (s, Si(CH$_3$)$_2$), −6.33 (s, SiPcCH$_3$). The compound is green and is soluble in CH$_2$Cl$_2$ and toluene. Solutions of it are rapidly photolyzed by white light.

To prepare HOSiPcOSi(CH$_3$)$_2$(CH$_2$)$_3$N(CH$_2$CH$_3$)(CH$_2$)$_2$ N(CH$_3$)$_2$, a mixture of the CH$_3$SiPcOSi(CH$_3$)$_2$(CH$_2$)$_3$N (CH$_2$CH$_3$)(CH$_2$)$_2$N(CH$_3$)$_2$ (300 mg, 0.38 mmol), toluene (600 mL) and (C$_2$H$_5$)$_3$N saturated with H$_2$O (2.2 mL) was irradiated with incandescent light (300 W projector lamp) for 40 minutes, and then concentrated on a rotary evaporator (~70° C.). The concentrate (~5 mL) was diluted with hexanes (2.5 mL) and filtered. The solid was washed (toluene), dissolved in CH$_2$Cl$_2$ (2 mL), precipitated from the solution with hexanes (20 mL), recovered by filtration, was washed (hexanes), vacuum dried (~90° C.), and weighed (136 mg, 0.17 mmol, 45%): UV-vis (toluene) λ$_{max}$ 670 nm; NMR (CD$_2$Cl$_2$, 7.6 mM) δ 9.28 (m, 1,4-Pc H), 8.30 (m, 2,3-Pc H), 1.93 (s, NCH$_3$), 1.77 (s, NCH$_2$CH$_2$N), 1.71 (q, NCH$_2$CH$_3$), 0.85 (m, γ-CH$_2$), 0.49 (t, NCH$_2$CH$_3$), −1.24 (m, β-CH$_2$), −2.43 (m, α-CH$_2$), −3.02 (s, SiCH$_3$). Anal. calculated for C$_{43}$H$_{44}$N$_{10}$O$_2$Si$_2$: C, 65.45; H, 5.62; N, 17.75. Found: C, 65.18; H, 5.51; N, 17.74. The compound is blue. It is soluble in toluene, CH$_2$Cl$_2$, dimethylformamide and ethanol.

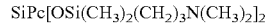  Compound XII

A mixture of CH$_3$OSi(CH$_3$)$_2$(CH$_2$)$_3$N(CH$_3$)$_2$ (201 mg, 1.1 mmol) and a suspension of SiPc(OH)$_2$ (232 mg, 0.40 mmol) and 2-ethylpyridine (30 mL) that had been dried by distillation (~1 mL of distillate) was slowly distilled for 1.5 hours (~11 mL of distillate). The resulting solution was filtered, and the filtrate was evaporated to dryness with a rotary evaporator (~40° C.). The solid formed was extracted (CH$_2$Cl$_2$-hexanes solution, 1:4, 15 mL), recovered from the extract by rotary evaporation (~40° C.), dissolved in $CH_2Cl_2$ (1.5 mL), precipitated from the solution with hexanes (18 mL), recovered by filtration, washed (hexanes), vacuum dried (~70° C.) and weighed (110 mg, 0.13 mmol, 33%): UV-vis (toluene) $\lambda_{max}$ 669 nm; NMR ($CDCl_3$) δ 9.61 (m, 1,4-Pc H), 8.31 (m, 2,3-Pc H), 1.55 (s, $NCH_3$), 0.80 (m, γ-$CH_2$), −1.14 (m, β-$CH_2$), −2.29 (m, α-$CH_2$), −2.89 (s, $SiCH_3$). MS-HRFAB exact mass, m/z: calculated for $C_{46}H_{53}N_{10}O_2Si_3$ $(M+H)^+$, 861.3661; found, 861.3627, 861.3638. The compound is blue and is soluble in $CH_2Cl_2$, dimethylformamide and toluene.

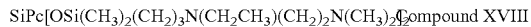
SiPc[OSi(CH₃)₂(CH₂)₃N(CH₂CH₃)(CH₂)₂N(CH₃)₂] Compound XVIII

A mixture of $CH_3OSi(CH_3)_2(CH_2)_3N(CH_2CH_3)(CH_2)_2N(CH_3)_2$ (191 mg, 0.77 mmol) and a suspension of $SiPc(OH)_2$ (144 mg, 0.25 mmol) and pyridine (45 mL) that had been dried by distillation (~9 mL of distillate) was slowly distilled for 1 hours (~3 mL of distillate) and then filtered. The filtrate was evaporated to dryness with a rotary evaporator (~80° C.), and the solid was extracted ($CH_2Cl_2$, 10 mL), recovered from the extract by rotary evaporation (~40° C.), washed twice (ethanol-water solution, 1:4), vacuum dried (~90° C.) and weighed (123 mg, 0.12 mmol, 48%): UV-vis (toluene) $\lambda_{max}$ 668 nm; NMR ($CDCl_3$) δ 9.64 (m, 1,4-Pc H), 8.33 (m, 2,3-Pc H), 2.03 (s, $NCH_3$), 1.91 (s, $NCH_2CH_2N$), 1.84 (q, $NCH_2CH_3$), 1.04 (m, γ-$CH_2$), 0.64 (t, $NCH_2CH_3$), −1.14 (m, γ-$CH_2$), −2.39 (m, α-$CH_2$), −2.89 (s, $SiCH_3$). MS-HRFAB exact mass, m/z: calculated for $C_{54}H_{70}N_{12}O_2Si_3$ $(M+H)^+$, 1003.5131; found, 1003.5085, 1003.5100. The compound is blue and is soluble in $CH_2Cl_2$, dimethylformamide and toluene.

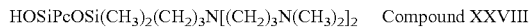
HOSiPcOSi(CH₃)₂(CH₂)₃N[(CH₂)₃N(CH₃)₂]₂     Compound XXVIII

To prepare $CH_3OSi(CH_3)_2(CH_2)_3N[(CH_2)_3N(CH_3)_2]_2$, a mixture of $CH_3OSi(CH_3)_2(CH_2)_3Cl$ (3.05 g, 18 mmol), $NH[(CH_2)_3N(CH_3)_2]_2$ (8.0 mL, 36 mmol), $K_2CO_3$ (0.488 g, 3.5 mmol) and $CH_3OH$ (1.0 mL) was heated in oil bath (~110° C.) for 48 hours and filtered. The filtrate was fractionally distilled under vacuum (5 mtorr) and a selected fraction (99-102° C.), was retained (543 mg): NMR ($CDCl_3$) δ 3.40 (s, $CH_3O$), 2.33 (m, $CH_2CH_2CH_2NCH_3$), 2.19 (s, $NCH_3$), 1.61 (quintet, $CH_2CH_2CH_2NCH_3$), 1.43 (m, β-$CH_2$), 0.55 (m, α-$CH_2$), 0.07 (s, $SiCH_3$). The product is a yellow oil.

All steps but the finally drying step of this procedure were carried out under low-intensity illumination. To prepare $CH_3SiPcOSi(CH_3)_2(CH_2)_3N[(CH_2)_3N(CH_3)_2]_2$, a mixture of the crude $CH_3OSi(CH_3)_2(CH_2)_3N[(CH_2)_3N(CH_3)_2]_2$ (322 mg) and a suspension of $CH_3SiPcOH$ (302 mg, 0.53 mmol) and pyridine (170 mL) that had been dried by distillation (~23 mL of distillate) was slowly distilled for 3 hours (~20 mL of distillate) and then filtered. The filtrate was evaporated to dryness on a rotary evaporator (~80° C.). The solid was washed (ethanol-water solution, 1:2) and chromatographed ($Al_2O_3V$, 3.5×15 cm³, ethyl acetate-$CH_3OH$ solution, 9:1) and the resulting solid was vacuum dried (~60° C.) and weighed (194 mg, 0.23 mmol, 43%): NMR ($CDCl_3$) δ 9.60 (m, 1,4-Pc H), 8.29 (m, 2,3-Pc H), 2.08 (s, $NCH_3$), 1.96 (t, $CH_2CH_2CH_2NCH_3$), 1.73 (t, $CH_2CH_2CH_2NCH_3$), 1.11 (quintet, $CH_2CH_2CH_2NCH_3$), 0.96 (m, γ-$CH_2$), −1.18 (m, β-$CH_2$), −2.46 (m, α-$CH_2$), −2.98 (s, $Si(CH_3)_2$), −6.39 (s, $SiPcCH_3$). The compound is green and is soluble in $CH_2Cl_2$ and toluene. Solutions of it are rapidly photolyzed by white light.

(Pc XXVII). A mixture of $CH_3SiPcOSi(CH_3)_2(CH_2)_3N[(CH_2)_3N(CH_3)_2]_2$ (180 mg, 0.21 mmol), toluene (360 mL), $(C_2H_5)_3N$ (18 mL) and $H_2O$ (1.5 mL) was irradiated with incandescent light (300 W projector lamp) for 25 minutes and then evaporated to dryness with a rotary evaporator (~35° C.). The solid was chromatographed ($Al_2O_3$, 3×14 cm³, ethyl acetate-$CH_3OH$ solution, 9:1) and the resulting solid was dissolved in $CH_2Cl_2$ (2 mL), precipitated from the solution with pentane (12 mL), recovered by filtration, washed ($CH_2Cl_2$-pentane solution, 1:6; pentane), vacuum dried (~60° C.) and weighed (74.3 mg, 0.086 mmol, 41%): UV-vis (dimethylformamide) $\lambda_{max}$ 668 nm; NMR ($CD_2Cl_2$, 6.7 mM) δ 9.14 (m, 1,4-Pc H), 8.12 (m, 2,3-PcH), 1.84 (s, $NCH_3$), 1.71 (t, $NCH_2CH_2CH_2NCH_3$), 1.47 (t, $CH_2CH_2CH_2NCH_3$), 0.83 (quintet, $CH_2CH_2CH_2NCH_3$), 0.64 (m, γ-$CH_2$), −1.41 (m, β-$CH_2$), −2.61 (m, α-$CH_2$), −3.17 (s, $SiCH_3$). MS-HRFAB exact mass, m/z: calculated for $C_{47}H_{53}N_{11}O_2Si_2$ $(M+H)^+$, 860.4001; found, 860.4020, 860.4011. The compound is blue and is soluble in $CH_2Cl_2$, dimethylformamide and toluene.

HOSiPcOSi(CH₃)₂(CH₂)₃NC₄H₈NCH₃     Compound XXVIII

To prepare $CH_3OSi(CH_3)_2(CH_2)_3NC_4H_8NCH_3$, a solution of $CH_3OSi(CH_3)_2(CH_2)_3Cl$ (3.09 g, 19 mmol), $HNC_4H_8N(CH_3)$ (4.0 mL, 36 mmol) and $CH_3OH$ (1.0 mL) was heated in an oil bath (~110° C.) for 22 hours and allowed to stand for 8 h. The resultant was decanted and the upper layer was retained (2.40 g): NMR ($CDCl_3$) δ 3.40 (s, $CH_3O$), 2.45 (m, $NCH_2CH_2N$), 2.32 (m, γ-$CH_2$), 2.26 (s, $NCH_3$), 1.51 (m, β-$CH_2$), 0.55 (m, α-$CH_2$), 0.08 (s, $SiCH_3$). The product is a yellow oil.

All steps but the finally drying step of this procedure were carried out under low-intensity illumination. To prepare $CH_3SiPcOSi(CH_3)_2(CH_2)_3NC_4H_8NCH_3$ A mixture of the crude $CH_3OSi(CH_3)_2(CH_2)_3NC_4H_8NCH_3$ (162 mg) and a suspension of $CH_3SiPcOH$ (201 mg, 0.35 mmol) and pyridine (90 mL) that had been dried by distillation (~9 mL of distillate) was slowly distilled for 3 hours (~10 mL of distillate) and then filtered. The filtrate was evaporated to dryness on a rotary evaporator (~80° C.). The solid was washed (ethanol-water solution, 1:4), vacuum dried (~60° C.) and weighed (252 mg, 0.33 mmol, 94%): NMR (7.3 mM, $CDCl_3$). δ9.61 (m, 1,4-Pc H), 8.31 (m, 2,3-PcH), 2.25 (s, $NCH_3$), 1.65 (m, $NCH_2CH_2N$), 0.90 (m, γ-$CH_2$), −1.25 (m, β-$CH_2$), −2.38 (m, α-$CH_2$), −2.98 (s, $Si(CH_3)_2$), −6.38 (s, $SiPcCH_3$). The compound is green and is soluble in $CH_2Cl_2$ and toluene. Solutions of it are rapidly photolyzed by white light.

A mixture of the $CH_3SiPcOSi(CH_3)_2(CH_2)_3NC_4H_8NCH_3$ (200 mg, 0.26 mmol), toluene (400 mL), $(C_2H_5)_3N$ (4.0 mL) and $H_2O$ (1.0 mL) was irradiated with incandescent light (300 W projector lamp) for 20 minutes, and then concentrated on a rotary evaporator (~70° C.). The concentrate (~5 mL) was diluted with hexanes (3.0 mL) and filtered. The solid was washed (toluene), dissolved in $CH_2Cl_2$ (6 mL), precipitated from the solution with hexanes (12 mL), recovered by filtration, washed (hexanes), vacuum dried (~60° C.), and weighed (82.9 mg, 0.11 mmol, 42%): UV-vis (dimethylformamide) $\lambda_{max}$ 668 nm; NMR ($CDCl_3$, 7.8 mM). δ 9.15 (m, 1,4-PcH), 8.18 (m, 2,3-PcH), 2.16 (s, $NCH_3$), 1.61 (m, $NCH_2CH_2N$), 0.76 (m, γ-$CH_2$), −1.37 (m, β-$CH_2$), −2.49 (m, α-$CH_2$), −3.10 (s, $SiCH_3$). MS-HRFAB exact mass, m/z: calculated for $C_{42}H_{40}N_{10}O_2Si_2$ $(M+H)^+$, 773.2953; found, 773.2944, 773.2950. The compound is blue and is soluble in $CH_2Cl_2$, dimethylformamide and toluene.

The following compounds were made in a fashion similar to that used for the above compounds.

SiPc[OSi(CH₃)₂(CH₂)₄NHSO₂CH₃]₂ Compound VIII A solution of $CH_3SO_2Cl$, $SiPc[OSi(CH_3)_2(CH_2)_4NH_2]_2$, $(C_2H_5)_3N$ and $CH_2Cl_2$ was stirred, and the product was isolated, chromatographed and recrystallized: MS-HRFAB exact mass, m/z: calculated for $C_{46}H_{52}N_{10}O_6S_2Si_2$ $(M)^+$, 988.2821; found, 988.2817, 988.2777.

HOSiPcOSi($CH_3$)$_2$($CH_2$)$_4$NHSO$_2$CH$_3$ Compound IX A mixture of CH$_3$ OSi($CH_3$)$_2$ ($CH_2$)$_4$NH$_2$, CH$_3$SiPcOH and pyridine was partially distilled and the resulting CH$_3$SiPcOSi($CH_3$)$_2$($CH_2$)$_4$NH$_2$ was isolated and recrystallized. A solution of this compound, CH$_3$SO$_2$Cl, ($C_2H_5$)$_3$N, and CH$_2$Cl$_2$ was stirred and the CH$_3$SiPcOSi($CH_3$)$_2$($CH_2$)$_4$NHSO$_2$CH$_3$ formed was isolated and chromatographed. Finally, a mixture of this intermediate, CH$_2$Cl$_2$, H$_2$O, and ($C_2H_5$)$_3$N was irradiated with light and the product was isolated, chromatographed, and recrystallized: MS-HRFAB exact mass, m/z: calculated for $C_{39}H_{35}N_9O_4SSi_2$ (M)$^+$, 781.2071; found, 781.2049, 781.2074.

SiPc[OSi($CH_3$)$_2$($CH_2$)$_4$NHCSNHC$_6$H$_{11}$O$_5$]$_2$ Compound XI A mixture of 2,3,4,6-tetra-O-acetyl-β-D-glucopyranosyl isothiocyanate, SiPc[OSi($CH_3$)$_2$($CH_2$)$_4$NH$_2$]$_2$ and benzene was refluxed and the resulting SiPc[OSi($CH_3$)$_2$($CH_2$)$_4$NHCSNHC$_{14}$H$_{19}$O$_9$]$_2$ was isolated. A solution of this compound and CH$_3$OH was treated with NH$_3$ gas and the product was isolated and recrystallized: MS-HRFAB exact mass, m/z: calculated for $C_{58}H_{70}N_{12}O_{12}S_2Si_3$ (M)$^+$, 1274.3986; found, 1274.3988, 1274.4024.

HOSiPcOSi($CH_3$)$_2$($CH_2$)$_3$OCOCH$_3$ Compound XIII A mixture of ClSi($CH_3$)$_2$($CH_2$)$_3$OCOCH$_3$, CH$_3$ SiPcOH and pyridine was refluxed, and the resulting CH$_3$SiPcOSi($CH_3$)$_2$($CH_2$)$_3$OCOCH$_3$ was isolated. A solution of this compound and toluene was irradiated with light and the product was isolated and recrystallized: MS-HRFAB exact mass, m/z: calculated for $C_{39}H_{32}N_8O_4Si_2$ (M)$^+$, 732.2085; found, 732.2100, 732.2084

SiPc[OSi($CH_3$)$_2$($CH_2$)$_3$N$^+$($CH_3$)$_2$($CH_2$)$_{11}$CH$_3$]$_2$2I$^-$ Compound XIV A solution of CH$_3$($CH_2$)$_{11}$I, SiPcOSi($CH_3$)$_2$($CH_2$)$_3$N($CH_3$)$_2$ and tetrahydrofuran was refluxed, and the product was isolated and recrystallized. Anal. calculated for $C_{70}H_{102}I_2N_{10}O_2Si_3$: C, 57.84; H, 7.07; I, 17.46; N, 9.64. Found: C, 58.19; H, 6.52; I, 17.40; N, 9.04, 9.63, 9.63.

($CH_3$)$_3$C($CH_3$)$_2$SiOSiPcOSi($CH_3$)$_2$($CH_2$)$_4$NCOC$_{27}$H$_{30}$N$_2$O Compound XV A solution of CH$_3$OSi($CH_3$)$_2$($CH_2$)$_4$NH$_2$, ($CH_3$)$_3$C($CH_3$)$_2$SiOSiPcOH and pyridine was partially distilled and the resulting ($CH_3$)$_3$C($CH_3$)$_2$SiOSiPcOSi($CH_3$)$_2$($CH_2$)$_4$NH$_2$ was isolated. A solution of this compound and CH$_2$Cl$_2$ was mixed with a mixture of rhodamine B base, (COCl)$_2$ and benzene which had been partially distilled, and the product was isolated and chromatographed: MS-HRFAB exact mass, m/z: calculated for $C_{72}H_{75}N_{11}O_4Si_3$ (M)$^+$, 1241.5311; found 1241.5295, 1241.5265.

HOSiPCOSi($CH_3$)$_2$($CH_2$)$_3$OH Compound XVII A solution of CH$_3$SiPcOSi($CH_3$)$_2$($CH_2$)$_3$OCOCH$_3$, CH$_3$OH, K$_2$CO$_3$ and CH$_2$Cl$_2$ was stirred, the reaction product was worked up, and the resulting CH$_3$SiPcOSi($CH_3$)$_2$($CH_2$)$_3$OH was isolated. A solution of this compound and toluene was irradiated with light and the product was isolated and chromatographed: MS-HRFAB exact mass, m/z: calculated for $C_{37}H_{30}N_8O_3Si_2$ (M)$^+$, 690.1979; found, 690.1982, 690.1966.

HOSiPcOSi($CH_3$)$_2$($CH_2$)$_3$NC$_4$H$_8$O Compound XIX A solution of CH$_3$OSi($CH_3$)$_2$($CH_2$)$_3$Cl, morpholine and CH$_3$OH was refluxed and the resulting CH$_3$OSi($CH_3$)$_2$($CH_2$)$_3$NC$_4$H$_8$O was isolated and distilled. A suspension of this compound, CH$_3$SiPcOH and pyridine was partially distilled, and the CH$_3$SiPcOSi($CH_3$)$_2$($CH_2$)$_3$NC$_4$H$_8$O was isolated and recrystallized. Finally, a mixture of this intermediate, toluene, ($C_2H_5$)$_3$N, and H$_2$O was irradiated with light, and the product was isolated and recrystallized: MS-HRFAB exact mass, m/z: calculated for $C_{41}H_{37}N_9O_3Si_2$ (M+H)$^+$, 760.2636; found, 760.2620, 760.2610.

AlPcOSi($CH_3$)$_2$($CH_2$)$_3$N$^+$($CH_3$)$_2$($CH_2$)$_{11}$CH$_3$I$^-$ Compound XXI A mixture of CH$_3$($CH_2$)$_{11}$I and AlPcOSi($CH_3$)$_2$($CH_2$)$_3$N($CH_3$)$_2$ was warmed, and the product was isolated and recrystallized: MS-HRFAB exact mass, m/z: calculated for $C_{51}H_{59}AlIN_9OSi$ (M)$^+$, 995.3472; found, 995.3444, 995.3428.

HOSiPcOSi($CH_3$)$_2$($CH_2$)$_8$N($CH_3$)$_2$ Compound XXII A solution of CH$_2$=CH($CH_2$)$_6$Br, ($CH_3$)$_2$NNH$_2$ and ether was stirred, the reaction mixture was worked up with HCl, NaNO$_3$, and NaOH, and the resulting CH$_2$=CH($CH_2$)$_6$N($CH_3$)$_2$ was isolated and distilled. A solution of this compound, ($CH_3$)$_2$SiHCl, CHCl$_3$, H$_2$PtCl$_6$xH$_2$O and isopropanol was warmed and the CH$_3$OSi($CH_3$)$_2$($CH_2$)$_8$N($CH_3$)$_2$—HCl formed was isolated. Next, a suspension of this intermediate, CH$_3$SiPcOH and pyridine was partially distilled, and the CH$_3$SiPcOSi($CH_3$)$_2$($CH_2$)$_8$N($CH_3$)$_2$ obtained was isolated and recrystallized. Finally, a solution of this compound and CH$_2$Cl$_2$ was irradiated with light and the product was isolated, chromatographed, and recrystallized: MS-HRFAB exact mass, m/z: calculated for $C_{44}H_{45}N_9O_2Si_2$ (M+H)$^+$, 788.3313; found, 788.3300, 788.3290.

SiPc[OSi($CH_3$)$_2$($CH_2$)$_3$NC$_4$H$_8$O$_2$ Compound XXIII A suspension of CH$_3$OSi($CH_3$)$_2$($CH_2$)$_3$NC$_4$H$_1$O, SiPc(OH)$_2$ and pyridine was partially distilled, and the product was isolated and recrystallized: MS-HRFAB exact mass, m/z: calculated for $C_{50}H_{56}N_{10}O_4Si_3$ (M)$^+$, 944.3794; found, 944.3750, 944.3780.

HOSiPCOSi($CH_3$)$_2$($CH_2$)$_3$NC$_4$H$_8$S Compound XXIV A solution of CH$_3$OSi($CH_3$)$_2$($CH_2$)$_3$Cl, thiomorpholine and CH$_3$OH was refluxed and the resulting CH$_3$OSi($CH_3$)$_2$($CH_2$)$_3$NC$_4$H$_8$S was isolated and distilled. A suspension of this compound, CH$_3$ SiPcOH and pyridine was partially distilled and the CH$_3$SiPcOSi($CH_3$)$_2$($CH_2$)$_3$NC$_4$H$_8$S formed was isolated and recrystallized. Finally, a mixture of this intermediate, toluene, ($C_2H_5$)$_3$N, and H$_2$O was irradiated with light, and the product was isolated, chromatographed and recrystallized: MS-HRFAB exact mass, m/z: calculated for $C_{41}H_{37}N_9O_2SSi_2$ (M)$^+$, 775.2330; found, 775.2308 7752310.

HOSiPcOSi($CH_3$)$_2$($CH_2$)$_3$N($CH_2$)$_3$CH$_3$)$_2$ Compound XXV A solution of CH$_3$OSi($CH_3$)$_2$Cl, ($CH_3$($CH_2$)$_2$)$_2$NH and CH$_3$OH was refluxed and the resulting CH$_3$OSi($CH_3$)$_2$($CH_2$)$_3$N(($CH_2$)$_3$CH$_3$)$_2$ was isolated. A suspension of this compound, CH$_3$SiPcOH and pyridine was partially distilled, and the product was isolated and chromatographed. Finally, a mixture of this intermediate, toluene, ($C_2H_5$)$_3$N, and H$_2$O was irradiated with light, and the product was isolated and recrystallized: MS-HRFAB exact mass, m/z: calculated for $C_{45}H_{47}N_9O_2Si_2$ (M+H)$^+$, 802.3470; found, 802.3434, 802.3435

HOSiPcOSi($CH_3$)$_2$($CH_2$)$_3$NCS Compound XXVI A mixture of CH$_3$OSi($CH_3$)$_2$($CH_2$)$_3$Cl, KNCS and dimethylformamide was warmed and the resulting CH$_3$OSi($CH_3$)$_2$($CH_2$)$_3$NCS was isolated. A mixture of the compound, CH$_3$SiPcOH and pyridine was partially distilled and the CH$_3$SiPcOSi($CH_3$)$_2$($CH_2$)$_3$NCS formed was isolated, recrystallized, and chromatographed. Finally, a solution of this intermediate and toluene was irradiated with light and the product was isolated and recrystallized: MS-HRFAB exact mass, m/z: calculated for $C_{38}H_{29}N_9O_2SSi_2$ (M)$^+$, 731.1704; found, 731.1696, 731.1669.

SiPc[OSi($CH_3$)$_2$($CH_2$)$_3$NC$_4$H$_8$NCH$_3$]$_2$ Compound XXX A suspension of CH$_3$OSi($CH_3$)$_2$($CH_2$)$_3$NC$_4$H$_8$NCH$_3$, SiPc(OH)$_2$ and pyridine was partially distilled, and the product was isolated and recrystallized: MS-HRFAB exact mass, m/z: calculated for $C_{52}H_{62}N_{12}O_2Si_3$ (M+H)$^+$, 971.4505; found, 971.4460, 971.4489.

HOSiPCOSi($CH_3$)$_2$($CH_2$)$_3$NC$_4$H$_8$N($CH_2$)$_3$CH$_3$ Compound XXXI A suspension of piperazine, CH$_3$($CH_2$)$_3$Br, toluene, and K$_2$CO$_3$ was refluxed, and the resulting HNC$_4$H$_8$N($CH_2$)$_3$CH$_3$ was isolated and distilled. A solution of this compound, CH$_3$OSi($CH_3$)$_2$($CH_2$)$_3$C$_1$ and CH$_3$OH was refluxed, and the $CH_3OSi(CH_3)_2(CH_2)_3NC_4H_8N(CH_2)_3CH_3$ formed was isolated. Next, a suspension of this intermediate, $CH_3SiPcOH$ and pyridine was partially distilled, and the $CH_3SiPcOSi(CH_3)_2(CH_2)_3NC_4H_8N(CH_2)_3CH_3$ obtained was isolated and chromatographed. Finally, a mixture of this compound, toluene $(C_2H_5)_3N$ and $H_2O$ was irradiated with light, and the product was isolated and recrystallized: MS-HRFAB exact mass, m/z: calculated for $C_{45}H_{46}N_{10}O_2Si_2$ $(M+H)^+$, 815.3422; found, 815.3424, 815.3423.

SiPc[OSi$(CH_3)_2(CH_2)_3NC_4H_8NH]_2$ Compound XXXII A solution of $CH_3OSi(CH_3)_2(CH_2)_3Cl$, piperazine and $CH_3OH$ was refluxed, and the resulting $CH_3OSi(CH_3)_2(CH_2)_3NC_4H_8NH$ was distilled. A suspension of this compound, SiPc$(OH)_2$ and pyridine was partially distilled and the product was isolated and recrystallized. MS-HRFAB exact mass, m/z: calculated for $C_{50}H_{58}N_{12}O_2Si_3$ $(M+H)^+$, 943.4192; found, 943.4160, 943.4213.

Preparation of PcIV Salts

HOSiPcOSi$(CH_3)_2(CH_2)_3N(CH_3)_2$(HCl). A mixture of a portion (1.0 mL) of an aqueous solution of HCl (10 N, 25 µL) and MeOH (7.5 mL), EtOH (40 mL), and HOSiPcOSi$(CH_3)_2$ $(CH_2)_3N(CH_3)_2$ (25 mg) was stirred for 10 min, evaporated to dryness with a rotary evaporator (room temperature), dissolved in $CH_2Cl_2$ (1.0 mL), recovered by the addition of MeCN (2.0 mL) and filtration, washed (pentane), chromatographed (Bio Beads SX-3, ethanol), air dried and weighed (17 mg, 67%). UV-vis (EtOH) $\lambda_{max}$, nm: 667; $^1H$ NMR (200 MHz, CDCl$_3$) δ 9.13 (m, 8 H), 8.22 (m, 8 H), 1.83 (d, 6 H), 1.21 (s, 1 H), 1.11 (m, 2 H), −1.19 (m, 2 H), −2.40 (t, 2 H), −3.05 (s, 6 H).

HOSiPcOSi$(CH_3)_2(CH_2)_3N(CH_3)_2(CH_3C(O)COOH)$. A mixture of pyruvic acid (4.7 mg), $CH_2Cl_2$ (26 mL) and HOSiPcOSi$(CH_3)_2(CH_2)_3N(CH_3)_2$ (12 mg) was stirred for 1 h, evaporated to dryness with a rotary evaporator, washed (MeCN, pentane), vacuum dried (60° C.) and weighed (8 mg, 59%). UV-vis (EtOH) $\lambda_{max}$, nm: 668 $^1H$ NMR (200 MHz, CDCl$_3$) δ 9.04 (m, 8 H), 8.20 (m, 8 H), 2.08 (s, 3 H), 1.79 (s, 6 H), 1.18 (t, 2 H), −1.31 (m, 2 H), −2.42 (t, 2 H), −3.10 (s, 6 H).

In Vitro Evaluation

Culture of Chinese Hamster V79-379 Cells

Chinese hamster V79-379 lung fibroblasts were grown in monolayer culture in McCoy's 5A medium (Gibco Laboratories, Grand Island, N.Y.) augmented with 10% calf serum and buffered with 20 mM HEPES (pH 7.4).

Uptake of Phthalocyanines

Total uptake was determined by scraping the phthalocyanine-treated monolayer, collecting the cells on a glass-fiber filter, and extracting the phthalocyanine in ethanol, as previously described by Ramakrishnan, et al., 1989. (Ramakrishnan, N., M. E. Clay, M. F. Horng, A. R. Antunez, & H. H. Evans, "DNA Lesions and DNA Degradation in Mouse Lymphoma L5178Y Cells After Photodynamic Treatment Sensitized by Chloroaluminum Phthalocyanine", *Photochem. Photobiol*, in press, 1989). The amount of drug was determined by absorption at 674 nm and expressed relative to the number of cells, as measured in a Coulter cell counter on an aliquot of the cell population. Controls included cells not treated with drug, medium alone, and drug-containing medium without cells. The results of the total uptake of the various compositions of the present invention in comparison to AlPcCl are set forth below in Table 1.

Drug Treatment and Light Exposure

The cells were treated with 1 µM AlPcCl (from Eastman Kodak, Rochester, N.Y.) or with phthalocyanine compositions I-VI (0.5-1.0 µM final concentration in the medium) for 18 hours by adding the appropriate volume of a 1.0 mM stock solution in dimethylformamide (DMF) to the culture medium. The growth medium was replaced with 4 mL Hank's balanced salt solution (HBSS), and the cells were irradiated. The light source was a 500 W tungsten-halogen lamp located approximately 29 inches below the surface of a glass exposure tray. The visible light administered to the cells was filtered to allow passage of only that portion of the visible spectrum above 600 nm (Lee Primary red filter No. 106, Vincent Lighting, Cleveland, Ohio). The fluence rate was approximately 0.074 kJ/m$^2$/s at the level of the cell monolayer.

Growth Delay

At the time of light exposure, there were approximately $1.5 \times 10^5$ cells per 25 cm$^2$ flask. Following irradiation, the HBSS was replaced by 10 mL of fresh complete growth medium, and the cultures were returned to the 37° C. incubator. At various times before and after irradiation, duplicate cultures were trypsinized and counted. Controls included untreated cells and cells treated with light alone or drug alone. In addition, in each experiment, the drug to be tested was compared to a standard treatment, i.e. 1 µM AlPcCl for 18 hours followed by 12 kJ/m$^2$ light. The results of the growth delay analysis for each of the compositions I-VI in comparison to AlPcCl are set forth in Table 1 below.

Clonogenic Cell Survival

Cells were irradiated at a density of approximately $2 \times 10^6$ per 25 cm$^2$ flask. Immediately after irradiation, the cell monolayer was treated with trypsin, and appropriate aliquots were plated in triplicate to give 100 to 200 colonies in each 10-cm Petri dish. Cell survival was determined by the ability of the cells to form colonies containing at least 50 cells. The response of cells treated with 1 µM AlPcCl and light was compared in each experiment.

TABLE 1

Activities of Several Al and Si Phthalocyanines

| | | | | Efficiency Relative to 1 µM (AlPcCl) | | |
|---|---|---|---|---|---|---|
| Comp. | Structure | Conc (µM) | Uptake | Growth Delay (12 kj/m$^2$) | $F_{10}$(AlPcCl)/ $F_{10}$(Pc) | $CF_{10}$(AlPcCl)/ $CF_{10}$(Pc) |
| | AlPcCl | 1.0 | 1.0 | 1.0 | 1.0 | 1.0 |
| I | AlPcOSi(CH$_3$)$_2$)CH$_2$)$_3$N(CH$_3$)$_2$ | 1.0 | 2.3 | 2.1 | 0.94 | 0.51 |
| II | AlPcOSI(CH$_3$)$_2$(CH$_2$)$_3$N(CH$_3$)$_3$$^+$I$^-$ | 1.0 | 1.8 | 3.4 | 0.99 | 0.72 |
| III | CH$^3$SiPcOSi(CH$_3$)$_2$(CH$_2$)$_3$N(CH$_3$)$_2$ | 1.0 | 0.07 | 0.05 | ND | ND |
| IV | HOSiPcOsi(CH$_3$)$_2$)(CH$_2$)$_3$N(CH$_3$)$_2$ | 0.5 | 1.3 | >3 | 1.85 | 3.9 |
| | | 1.0 | 1.64 | ND | 4.25 | 3.5 |
| V | HOSiPcOSi(CH$_3$)$_2$(CH$_2$)$_3$N(CH$_3$)$_3$$^+$I$^-$ | 1.0 | 0.3 | 0 | 0.59 | 3.0 |
| VI | SiPc(OSi(CH$_3$)$_2$(CH$_2$)$_3$N(CH$_3$)$_3$)$^+$I$^-$)$_2$ | 1.0 | 0.1 | 0.5 | ND | ND |

Results of Testing Compounds I-VI in V79-379 Cell Culture

All of the compounds have been examined for the extent of cellular uptake after exposure of V79 cells to 1 μM or less in complete medium, and the data of Table 1 are presented relative to the uptake from 1 μM AlPcCl, which was 0.723±0.172 nmole/$10^7$ cells (mean±S. D., 25 determinations). Compounds I, II, and IV were taken up into the cells more efficiently than was AlPcCl under these conditions. In particular, when the concentration of Compound IV was 1 μM in the medium, the uptake into the cells was sufficiently high that some of the uptake and phototoxicity studies were repeated at 0.5 μM. Compounds III, V, and VI were less effectively incorporated into V79 cells.

Photodynamic action against V79 cells was assessed both by measurement of growth delay and by assay of the loss of clonogenicity. With both assays, none of the compounds showed any dark toxicity at concentrations of 1.0 μM or less for up to 18 hours.

The inhibition of V79 culture growth was measured during a three day period following red light irradiation (12 kJ/$m^2$) of phthalocyanine-pretreated cells. With each of the active compounds, as well as with AlPcCl, there was an initial decrease in cell density, as dead cells became detached from the monolayer. Thereafter, the cell number per flask increased, as living cells grew and divided. The time for the cell density to recover to the level at the time of light exposure was considered the growth delay. Cells treated with 1 μM AlPcCl for 18 hours and 12 kj/$m^2$ light were used for comparison purposes in each experiment and demonstrated a growth delay of approximately 24 hours. The ratio of the growth delay for the test photosensitizer and the growth delay for AlPcCl measured in the same experiment is recorded in Table 1. There was less inhibition of culture growth when cells were exposed to compounds III, V, or VI as expected from the poor cellular uptake of these drugs. In contrast, substantial inhibition was observed for compounds I, II, and IV. A value of >3 for compound IV (Table 1) indicates that the cell density had not recovered to the initial level during the three day observation period.

Photocytotoxicity of the phthalocyanines compounds I to VI was also assessed by clonogenic assay (Table 1, FIG. 1). In all experiments, 1 μM AlPcCl was included for comparison purposes. From the survival curves (FIG. 1), the fluence reducing the cell survival to 10% ($F_{10}$) was obtained. The ratio of the $F_{10}$ for AlPcCl and the $F_{10}$ for the test compound is recorded in Table 1. Compounds I and II appear to be nearly as efficient photosensitizers as AlPcCl, while compound IV (assayed at half the concentration) was almost twice as efficient as the standard AlPcCl. Clonogenic assays were not conducted for compounds III and VI, since the data on uptake and growth delay suggested that these compounds would have poor activity. However, in spite of the low efficiency of compound V in inhibiting cell growth, survival measurements were made for this compound, because it was taken up into V79 cells somewhat more efficiently than compounds III and VI.

Figure 2:
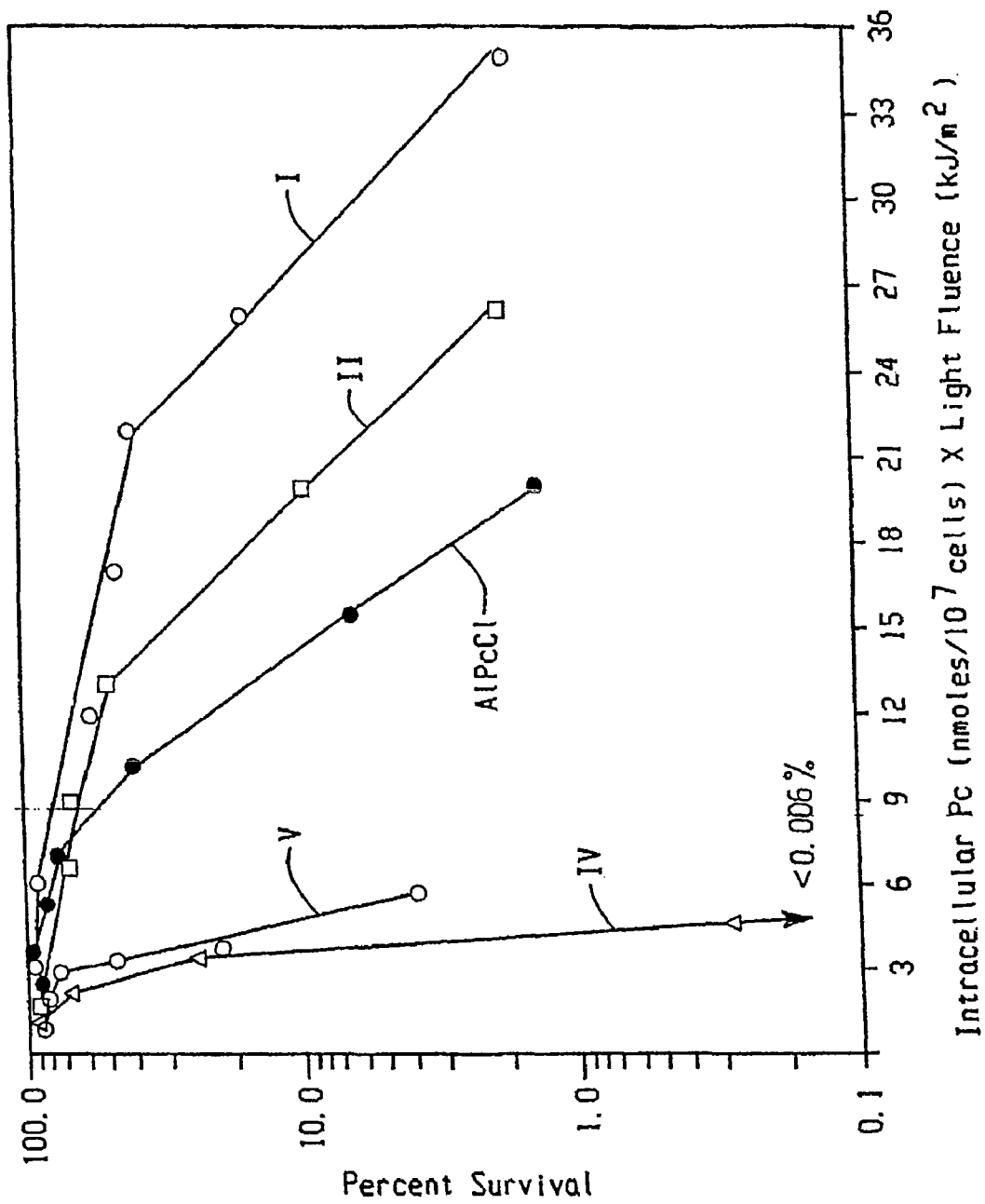
FIG. 2 is a graph demonstrating the percent survival of the compositions of the present invention in comparison to ALPcCl in relation to intracellular phthalocyanine (nmole/ $10^7$ cells) and light fluence ($kJ/m^2$). In this regard, in FIG. 2 the data of FIG. 1 were replotted as a function of the product of the amount of cell-associated phthalocyanine and the light fluence.

In order to take differences in cellular uptake into consideration in the assessment of the relative efficiency of these phthalocyanines as photosensitizers of V79 cells, the survival data were replotted against the product of intracellular phthalocyanine concentration and light fluence (FIG. 2). From these curves, the product of intracellular concentration and light fluence reducing survival to 10% ($CF_{10}$) was obtained, and comparisons of the values for AlPcCl and the test compounds are recorded in Table 1. By this and the other criteria, compound IV appears to be the most efficient photosensitizer.

However, when consideration is given to the lesser cell uptake of compound V, it appears to be about as strong a photosensitizer as compound IV.

Discussion of Testing Compounds I-VI in V79 Cell Culture Photocytotoxicity

The low activity of compounds III and VI appears to be due to poor cell uptake. Both of these compounds have functional groups on both faces of the phthalocyanine ring, and it is possible that one face of the ring must be free for proper interaction with target biomolecules. Either Si phthalocyanine with no more than a hydroxyl group on one face (IV) or Al phthalocyanine with one face free of substituents (I and II) allows efficient cellular uptake as well as a high degree of cellular inactivation. Thus, both tertiary and quaternary amines appear to be efficacious structures. Compound V is an anomaly. Although it has features on either face of the phthalocyanine ring found on active molecules, the combination appears not to allow efficient cellular uptake. However, that which is incorporated into the cells has good photodynamic activity.

The results of the in vitro biological tests of the new phthalocyanines compounds I to VI are an important introduction to the design of a new class of photosensitizers. The results suggest that tertiary and quaternary amines may be an important class of structures to be explored. The axial ligands of the series of compounds listed in Table 1 are simpler than the corresponding ligand of the original diethylamine which served as a prototype. The simpler ligands appear to have the advantages of stability in solution, making them easier to study. The instability of the diethylamine precluded precise measurements of the concentration of the active species at the time of irradiation. Therefore, the true photosensitizing activity of the prototype compound may also be high.

Evaluation and Uptake of Phthalocyanine Compounds VII-XV, XVII-XIX, XXI-XXVIII, and XXX-XXXII In addition to the phthalocyanine compounds I to VI, several other new phthalocyanine compounds have proven to be effective in treating cancer. V79 cells Chinese hamster lung fibroblasts were cultured using the cell culture methods described above. The phthalocyanines listed in table 2 were added to the cultures typically at concentrations of 1 μM, 2 μM, and/or 4 μM and incubated for 18 hours, after which aliquots of the cells were counted and other aliquots were collected on a glass fiber filter. When the filters were dry, the phthalocyanines were extracted into ethanol and the absorption determined at the peak wavelength, usually 668 nm. Values were converted to nmoles taken up by $10^6$ cells, using an extinction coefficient of $2.93 \times 10^5$. The cellular uptake of the phthalocyanines are presented in Table 2.

TABLE 2

Uptake of Additional Phthalocyanines Into V79 Cells

| Pc Num. | n Moles/$10^6$ cells | | | n Moles/$10^6$ Cells/μM |
|---|---|---|---|---|
| | 1 μM | 2 μM | 4 μM | |
| IV | 0.7 ± 0.2 | 3.1 ± 0.3 | 4.6 ± 2.9 | 1.1 |
| VII | 0.2 ± 0.03 | | 1.1 ± 0.5 | 0.2 |
| VIII | 0.1 ± 0.04 | | 0.8 ± 0.01 | 0.2 |
| IX | 0.1 ± 0.1 | | 1.8 ± 0.8 | 0.3 |
| X | 0.6 ± 0.2 | | 3.3 ± 1.4 | 0.7 |
| XI | 0.1 | | 0.3 ± 0.1 | 0.1 |
| XII | 2.1 ± 1.2 | | 4.6 ± 1.5 | 1.6 |
| XIII | | | 1.7 ± 0.3 | 0.4 |
| XIV | 0.03 ± 0.01 | | 0.05 ± 0.01 | <0.05 |
| XV | 0.01 ± 0.01 | | 0.14 ± 0.12 | <0.05 |
| XVI | 0.2 ± 0.2 | | 0.7 ± 0.20 | 0.2 |

TABLE 2-continued

Uptake of Additional Phthalocyanines Into V79 Cells

| Pc Num. | n Moles/10⁶ cells | | | n Moles/10⁶ Cells/μM |
|---|---|---|---|---|
| | 1 μM | 2 μM | 4 μM | |
| XVII | | | 1.7 ± 0.2 | 0.4 |
| XVIII | 0.3 ± 0.1 | | 3.6 ± 0.6 | 0.3* |
| XIX | 0.3 ± 0.1 | | 2.4 ± 0.5 | 0.3* |
| XXI | 1.2 ± 0.2 | | 5.8 ± 0.4 | 1.3 |
| XXII | | | | ND |
| XXIII | | | | ND |
| XXIV | 0.003 ± 0.001 | | 1.3 ± 0.1 | <0.05* |
| XXV | 0.02 ± 0.02 | | 1.5 ± 0.3 | <0.05* |
| XXVI | | | | ND |
| XXVII | 1.8 | | 5.0 ± 0.01 | 1.5 |
| XXVIII | 1.2 ± 0.2 | 3.6 ± 1.0 | 11.4 ± 0.05 | 1.2* |
| XXX | | | | ND |
| XXXI | | 0.61 ± 0.1 | | 0.3 |

In the last column, wherever possible, a composite value was calculated, in order to have a single number for the purposes of ranking the uptake efficiency of the compounds. For most compounds, the average of all the data has been calculated and rounded to the first decimal. Where all values are <0.05, the data are presented as <0.05. An asterisk (*) indicates that an average uptake value, which is the average of the phthalocyanine doses would be higher than the listed value which is for 1 μM.

It appears from Table 2 that the uptake of PcXVIII, PcXIX, PcXXIV, PCXXV, and PcXXVIII are not linearly dependent upon the phthalocyanine concentration in the medium. PcIV, PcXII, PcXXI, PcXXVII and PcXXVIII are taken up particulary well by the V79 cells.

Clonogenicity Studies Using Phthalocyanine Compounds VII-XV, XVII-XIX, XXI-XXVIII, and XXX-XXXII into V79 Cells Using the cell culture methods described above, V79 cells Chinese hamster lung fibroblasts were treated with either 0.5 or 1.0 μM of the phthalocyanines listed in Table 3. About 18 hours thereafter, the cells were irradiated with increasing doses of 675 nm broad band red light from a 500 W tungsten-halogen lamp fitted with a 600 nm high pass filter, to determine the light dosage that would kill 90% of the phthalocyanine treated cells. Where 90% of the cells were not killed, the maximum percent of cells killed were determined, (expressed as % survival) and the related light dosage recorded. The results are presented in Table 3.

TABLE 3

EVALUATION OF PHTHALOCYANINE COMPOUNDS IN KILLING V79 CELLS USING PHOTODYNAMIC THERAPY

| Pc | Concn μM | LD 90 (kj/m²) | Maximum Effect (% survival at kj/m²) | n Moles/10⁶ cells/μM (from Table 2) |
|---|---|---|---|---|
| IV | 0.5 | 4 | | 1.1 |
| VII# | 0.5 | 4 | | 0.2 |
| VIII | 1 | | 94% at 30 | 0.2 |
| IX | 0.5 | | 44% at 9 | 0.3 |
| X | 0.5 | 7 | | 0.7 |
| XI | 1 | | 100% at 20 | 0.1 |
| XII | 0.5 | 3.3 | | 1.6 |
| XIII | 1 | | 88% at 15 | 0.4 |
| XIV | 1 | | 93% at 10 | <0.05 |
| XV | 4 | | 81% at 20 | <0.05 |
| XVI | 4 | | 100% at 10 | 0.2 |
| XVII | 1 | | 19% at 10 | 0.4 |
| XVIII | 1 | 7 | | 0.3* |
| XIX | 1 | | 81% at 10 | 1.3 |
| XXI | 0.5 | 15* | | ND |
| XXII | 0.5 | 10 | | ND |
| XXIV | 0.5 | | 100% at 10 | <0.05* |
| XXV | 0.5 | | 87% at 8 | <0.05* |
| XXVI | 1 | | 100% at 30 | ND |
| XXVII | 0.5 | 6.8 | | 1.5 |
| XXVIII | 0.5 | 1.8 | | 1.2* |
| XXX | | | 30% at 10 | ND |
| XXXI | 0.5 | | 30% at 10 | 0.3 |

*not totally soluble at 0.5 mM
Preplated data only

As shown in Table 3, PcIV, PcVII, PcXII, and PcXXVIII achieved the LD 90 at the lowest light dosage, and thus are the most active photsensitizers, that is they are the most active at killing V79 cells.

For comparison, the phthalocyanine uptake values presented in Table 2 were also presented in the last column of Table 3. As shown in Table 3, some, but not all, of the differences in photosensitizing activity among phthalocyanines can be explained by differences in uptake. For example, PcXXVIII which has the highest activity in killing V79 cells of all of the phthalocyanines also has a high uptake. The uptake of PcXXVIII at 1 μM is less than that for PcXII, whereas its photodynamic killing efficiency is superior to PcXII when analyzed at 0.5 μM.

It is not surprising that often phthalocyanines with poor uptake are relatively less active in photodynamic therapy, whereas the most active phthalocyanines demonstrate a relatively high uptake. However, uptake and activity are not always correlated. For example, PcVII has poor uptake but one of the better photosensitizers. PcXIX has poor uptake but is less active as a photosensitizer, whereas PcXVIII, with similar uptake, demonstrated good activity. Many factors contribute to determination of the photosensitizer efficiency, including physical state in the cells and localization.

Assessment of Photodynamic Efficiency of Additional Phthalocyanines in L5178Y-R Cells Mouse lymphoma L5178y-R (hereinafter also referred to as "LY-R") cells were grown in suspension culture as described in Ramakrishnan N., Oleinick, N. L. Clay, M. E., Homg, M. F., Antunez, A. R., and Evans H. H., Photochem. Photobiol. 50, 373-378, 1989 and Agarwal, M. L., Clay, M. E., Harvey, E. J., Evans, H. H., Antunez, A. R., and Oleinick, N. L., Cancer Res., 51, 5993-5996, 1991.

The cells were used while in exponential growth. Stock solutions of either 0.5 or 1 mM of PcIV, PcXII, PcX, PcXVIII were prepared in dimethylformamide unless otherwise indicated and added to the 10 mL medium at a rate of 1 μL per mL. After allowing 18 hours for uptake of the phthalocyanine into the cells, the flasks containing the cultures were placed on a glass exposure tray above a 500-W tungsten-halogen lamp. The exposure tray was fitted with a 600-nm high-pass filter. Flasks were exposed to various fluences of red light (up to 30 kJ/m²) at a fluence rate of approximately 74 W/m²). After irradiation, the cells were collected by centrifugation.

For measurement of clonogenic cell survival, aliquots were plated in medium containing soft agar as described in Ramakrishnan N., Oleinick, N. L. Clay, M. E., Homg, M. F., Antunez, A. R., and Evans H. H., Photochem. Photobiol. 50, 373-378, 1989. The aliquots were plated in sufficient numbers to produce 50-200 colonies. The dishes were kept in an incubator at 37° C. in an atmosphere of 5% $CO_2$ and 95% air for 10-14 days to allow viable cells to form colonies. Colonies were counted by eye. Controls treated with the phthalocyanine alone had plating efficiencies of about ~90%. The plating efficiencies of the treated cells are normalized to the plating efficiencies of control cells in each experiment. For measurement of the induction of apoptosis, DNA was isolated from the treated and control cells 2 hours after photodynamic therapy, subjected to electrophoresis on 1.5% agarose, stained with ethidium bromide, and visualized by UV transillumination, as described in Agarwal et al. The results are shown in Tables 4, 5 and 6 and in FIG. 3.

TABLE 4

Comparison of Different Phthalocyanine Compounds In PDT-treated LY-R cells

| LIGHT DOSE ($kJ/m^2$) | Pc IV | | Pc XII | | Pc X | | Pc XVIII | |
|---|---|---|---|---|---|---|---|---|
| | AVG. | SD | AVG. | SD | AVG. | SD | AVG. | SD |
| 0 | 100 | | 100 | | 100 | | 100 | |
| 1 | 80.9 | 11.4 | 82.2 | 8.6 | | | | |
| 2 | 19.7 | 2.9 | 5.23 | 0.86 | 71.8 | 15.4 | 81.8 | 6.0 |
| 2.5 | 0.82 | 0.09 | 0.90 | 0.15 | | | | |
| 3 | 0.16 | 0.10 | 0.15 | 0.01 | 30.1 | 3.7 | 73.6 | 4.8 |
| 4 | | | 0.014 | 0.002 | 20.5 | 1.1 | 64.0 | 7.0 |
| 5 | 0.014 | 0.001 | 0.0027 | 0.0008 | 0.43 | 0.19 | 52.1 | 6.2 |
| 6 | | | | | 0.031 | 0.014 | 33.8 | 5.8 |
| 8 | | | | | 0.00058 | 0.0003 | 9.13 | 1.52 |
| 10 | | | | | | | 3.0 | 3.0 |

In Table 4 each phthalocyanine was present at 0.5 µM, and the normalized plating efficiencies are presented as mean and standard deviation at each fluence tested. The results show that all four phthalocyanines are active photosensitizers for photodynamic therapy. Based on their relative ability upon irradiation with various fluences of red light to reduce tumor cell survival, these phthalocyanines are ranked from the most active photosensitizers to the least active: PcIV, PcXII, PcX, PcXVIII. This relative activity of these four phthalocyanines is the same as obtained from screening in V79 cells.

Figure 3:
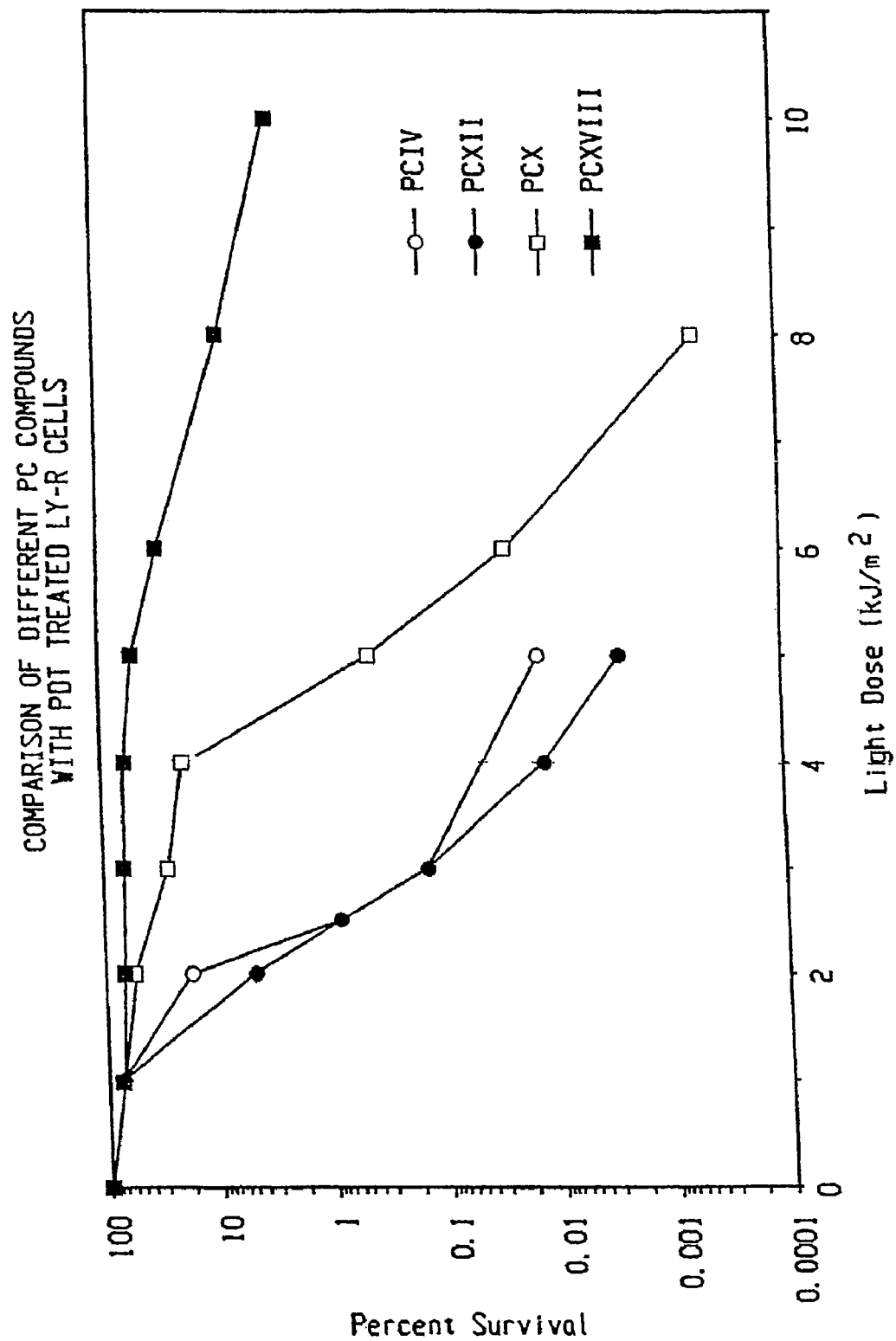
FIG. 3 is a graph which compares the percent survival of L5178Y strain R cells receiving photodynamic therapy and treated with: PcIV, represented by the open circles; PcXII, represented by the solid circles; PcX, represented by the open squares; and PcXVIII, represented by the solid squares, at varying doses of light.

FIG. 3 shows the average plating efficiencies from Table 4 plotted against the fluence for each Pc.

TABLE 5

Clonogenic Assay of Phthalocyanines

| Pc | Concentration (µM) | $Ld_{50}$ ($kJ/m^2$) | $Ld_{90}$ ($kJ/m^2$) |
|---|---|---|---|
| Pc IV | 0.5 µM | 1.38 | 2.15 |
| Pc X | 0.5 µM | 2.38 | 4.19 |
| Pc XII | 0.5 µM | 1.11 | 1.70 |
| Pc XVIII | 0.5 µM | 5.00 | 7.81 |

Table 5 shows the fluence that reduces the cell survival to 50% and to 10% and which are given as $LD_{50}$ and $LD_{90}$, respectively. The most active compound of the phthalocyanines shown in Table 5 is PcXII. PcXII when present in the culture medium at 0.5 µM requires less light, that is the lowest fluence, to kill either 50% or of the cells. PcIV is about 80% as active as PcXII, PcX is 44% as active as PcXII and PcXVIII is 22% as active as PcXII.

TABLE 6

Relative Capacity of Phthalocyanines to Induce Apoptosis

| | Minimum Demonstrated Condition | | |
|---|---|---|---|
| Pc | Concentration (µM) | Fluence ($kJ/m^2$) | C × F $Ld_{90}$ ($kJ/m^2$) |
| Pc IV | 0.4 | 3.0 | 1.2 |
| Pc VII | 0.5 | 3.0 | 1.5 |
| Pc IX | 0.3 | 12.0 | 3.6 |
| | 0.5 | 8.0 | 4.0 |
| | 1.0 | 12.0 | 12.0 |
| Pc X | 0.5 | 6.0 | 3.0 |
| | 1.0 | 3.0 | 3.0 |
| Pc XII | 0.4 | 3.0 | 1.2 |
| Pc XVIII | 0.5 | 10.0 | 5.0 |

TABLE 6-continued

Relative Capacity of Phthalocyanines to Induce Apoptosis

| | Minimum Demonstrated Condition | | |
|---|---|---|---|
| Pc | Concentration (µM) | Fluence ($kJ/m^2$) | C × F $Ld_{90}$ ($kJ/m^2$) |
| | 1.0 | 3.0 | 3.0 |
| Pc XXII | 0.5 | 10.0 | 5.0 |
| Pc XXVIII | 0.3 | 3.0 | 0.9 |
| Pc XXX (DMF-Tween 80) | 0.5 | 15.0 | 7.5 |
| Pc XXXII (DMF-Tween 80) | 0.5 | 5 | 2.5 |

Table 6 shows that photodynamic therapy with the phthalocyanine compounds listed causes L5178Y cells to undergo apoptosis as the mode of cell death. Cells were treated with various concentrations of the compounds listed in the table and various light fluences. DNA gels were prepared and examined for the characteristic "ladder" pattern of DNA fragments. For each Pc, the minimum total PDT dose tested (calculated as the product of the minimum phthalocyanine concentration and the minimum fluence) which produced visible DNA fragments is recorded. PcXXX and PcXXXII were not soluble in DMF and were suspended and partially solubilized in DMF/Tween 80 for this assay. PcIX is unusual in that its activity increases and then decreases as the concentration is raised. PcX was added at concentrations of 0.5 and 1.0 µM; the same minimum value for the CxF product was obtained in both cases. PcXVIII was also added at 0.5 and 1.0 µM. The minimum value of CxF differed only slightly for the two conditions. PcV, PcVI, PcVIII, PcXI, PcXIV and PcXV, when evaluated at a concentration of 1 μM at a fluence of 30 kJ/m² did not induce apoptosis. Compound PcXVI at a concentration of 4 μM and a fluence of 20 kJ/m² for 2 hours did not induce apoptosis.

In Vivo Evaluation of Phthalocyanine Compounds VII-XV, XVII-XIX, XXI-XVII, and XXX-XXXII The relative effectiveness at reducing tumor volume of selected phthalocyanine compounds at a given dosage was compared in vivo. RIF-1, i.e., radiation-induced fibrosarcoma, tumors were implanted into the backs of C3H/HeN mice. One tumor was implanted per mouse. Each of the phthalocyanine compounds listed in Table 7 was sonicated and vortexed in corn oil to produce a suspension. When the tumors reached 5-7 cm in diameter and 2-3 mm in thickness, each mouse received 1 mg/kg in 0.1 mL of the corn oil, of the phthalocyanine suspension. For comparison, select mice received a conventional photosensitizer; either 5 mg/kg of chloroaluminum phthalocyanine tetrasulfonate, herein also referred to as "AlPcTS" in phosphate buffered saline or 5 mg/kg of Photofrin®-II in 5% dextrose. Twenty-four hours after the photosensitizers were administered, the tumors were irradiated with visible radiation delivered by an argon-pumped dye laser. The mice that received a phthalocyanine photosensitizer received light having a wavelength of 675 nm and the mice that received the Photofrin® II photosensitizer received light having a wavelength of 630 nm. Each tumor received 135 J/cm² of radiation. Tumor size was measured every day using calipers. The initial tumor volume was 50±10 mm³. Tumor volume was calculated according to the hemiellipsoid model by the formula:

$$V = \frac{1}{2}(4\pi)/3 \times (\frac{1}{2} \times (w/2)) \times h$$

Where l is length
Where W is width
Where H is height
The tumor response is shown in Table 7.

TABLE 7

Comparative Responses of RIF-1 Implanted Tumors to PDT With Selected Phthaocyanine Compounds

| Photosensitizer | Tumor Responses at 24 hours | Doubling Time of Initial Tumor Volume after PDT in days |
|---|---|---|
| Pc XXXVIII | complete | 24 |
| Pc XII | complete | 20 |
| Pc IV | near complete | 16 |
| Pc XVIII | near complete | 12 |
| Pc IX | near complete | 11 |
| Pc V | moderate | 6 |
| Pc VIII | slight | 4 |
| AlPcTS* | substantial | 7 |
| Photofrin ™-II | near complete | 12 |
| controls | | 4 | complete—no evidence of any tumor mass in any animal; only the scar from the photodynamic therapy was evident.
near complete—evidence of any tumor mass in four or five animals; only some tumor mass in one or two animals.
substantial—a significant tumor shrinkage occurred in all animals. In some animals the tumor response was complete, yet in others the response was not complete.
moderate—some tumor shrinkage was evident in some animals. In animals with some tumor shrinkage, scar formation was evident.
slight—some tumor decrease occurred in one or two mice.

While the tumor volume in the control mice doubled in four days, the doubling of tumor volume was delayed in the animals treated with each of the compounds except PcVIII. PcXXVIII, PcXII, PcIV, PcXVIII, PcIX were particularly effective in reducing tumor volume.

Histological examination of tumors treated with PcIV revealed the presence of apoptotic bodies in the tumor. Analysis of tumors treated with PCIV showed DNA fragments whose sizes were multiples of 180-200 base pairs.

As can be seen from Table 7, PcXXVIII, PcXII and PcIV significantly impair the growth of the tumors and are the most preferred photosensitizers for the treatment of cancer, because of effectiveness at set dosage of phthalocyanine.

Not only do the phthalocyanine compounds of the present invention reduce tumor volume, they are capable of eliminating tumors completely particularly upon multiple exposures to radiation.

Complete Inhibition of Tumors by PDT with PcIV

As occurs with PF-II-PDT, regrowth of tumors from the tumor margins occurred in the animals treated PcIV, followed by the exposure to light. This regrowth possibly originates from the cells which somehow escape irradiation.

To overcome the regrowth, RIF-1 tumors were implanted in C3H/HeN mice, and the mice were treated with PcIV followed by multiple exposures to light. For multiple exposures to light to be successful, the tumor tissue must retain sufficient levels of the photosensitizer over the exposure period.

Since phammacokinetic data indicated that Pc IV is retained in tumor tissue even after 7 days of its administration, Pc IV was administered once at the dose of 1 mg/kg body weight in corn oil or entrapped in DPPC liposomes. Thereafter, the tumors were irradiated with an argon ion pumped dye laser tuned at 675 nm for the total light dose of 135 J/cm² (75 mW/cm²). The tumors were irradiated with multiple exposures of 675 nm laser light, at varying times, as shown in Table 8.

TABLE 8

Responses of RIF-1 implanted tumors to PcIV followed by multiple exposures to light

| day of exposure | % of Mice Surviving | | |
|---|---|---|---|
| | corn oil 15 days | liposomes 30 days | liposomes 120 days |
| 2 | 100 | 100 | N/A |
| 2 and 3 | 100 | 100 | N/A |
| 2, 3, and 4 | 100 | 0 | 0 |
| 2, 3, 4, 5, and 6 | 100 | 0 | 0 |
| 2-6 | 100 | 0 | 0 |
| 2 and 7 | 100 | 100 | N/A |

Where Pc IV was given in corn oil, regrowth of tumors was evident 15 days after photodynamic therapy in all the multiple exposure protocols. However, when the PcIV was administered entrapped in DPPC liposomes, complete tumor cure was evident in those mice which were irradiated three, four or five times at an interval of 24 hours. No tumor regrowth occurred even at 120 days after the photodynamic therapy. Indeed, at the time the mice were sacrificed 300 days after the light treatment, there was no evidence of tumor regrowth. Tumor regrowth occurred 30 days after photodynamic therapy only in those animals which were irradiated only one or two times either at 24 or 120 hour intervals. One reason for this differential effect may be related to the pharmacokinetics of the dye, that is the dye may have been retained in the tissue for a long period which permitted multiple exposures to be effective. Alternatively, the administration of Pc IV, via DPPC liposomes may enhance uptake and retention of PcIV by the tumor cells.

Treatment of Chemically Induced Skin Tumors 6-week-old female SENCAR mice received a single topical application of 5 μg DMBA in 0.2 mL acetone on the dorsal skin as tumor initiator. One week later, the animals were started on twice-weekly topical applications of 1 μg TPA in 0.2 mL acetone as tumor promoter. All of the animals developed tumors at 12 weeks. Mice that developed 4-5 tumors per animal averaging 5-8 mm in diameter and 2-5 mm in thickness were used. Pc IV, entrapped in DPPC liposomes was administered intraperitoneally at doses of either 0.5 or 1.0 mg/kg and 24 hrs later the tumor area was illuminated with light from an argon pumped dye laser tuned at 675 nm for a total light dose of 135 j/cm$^2$ (75 mW/cm$^2$). All possible controls were included; either the animals were untreated, treated only with laser light or treated only with Pc IV alone.

Figure 4:
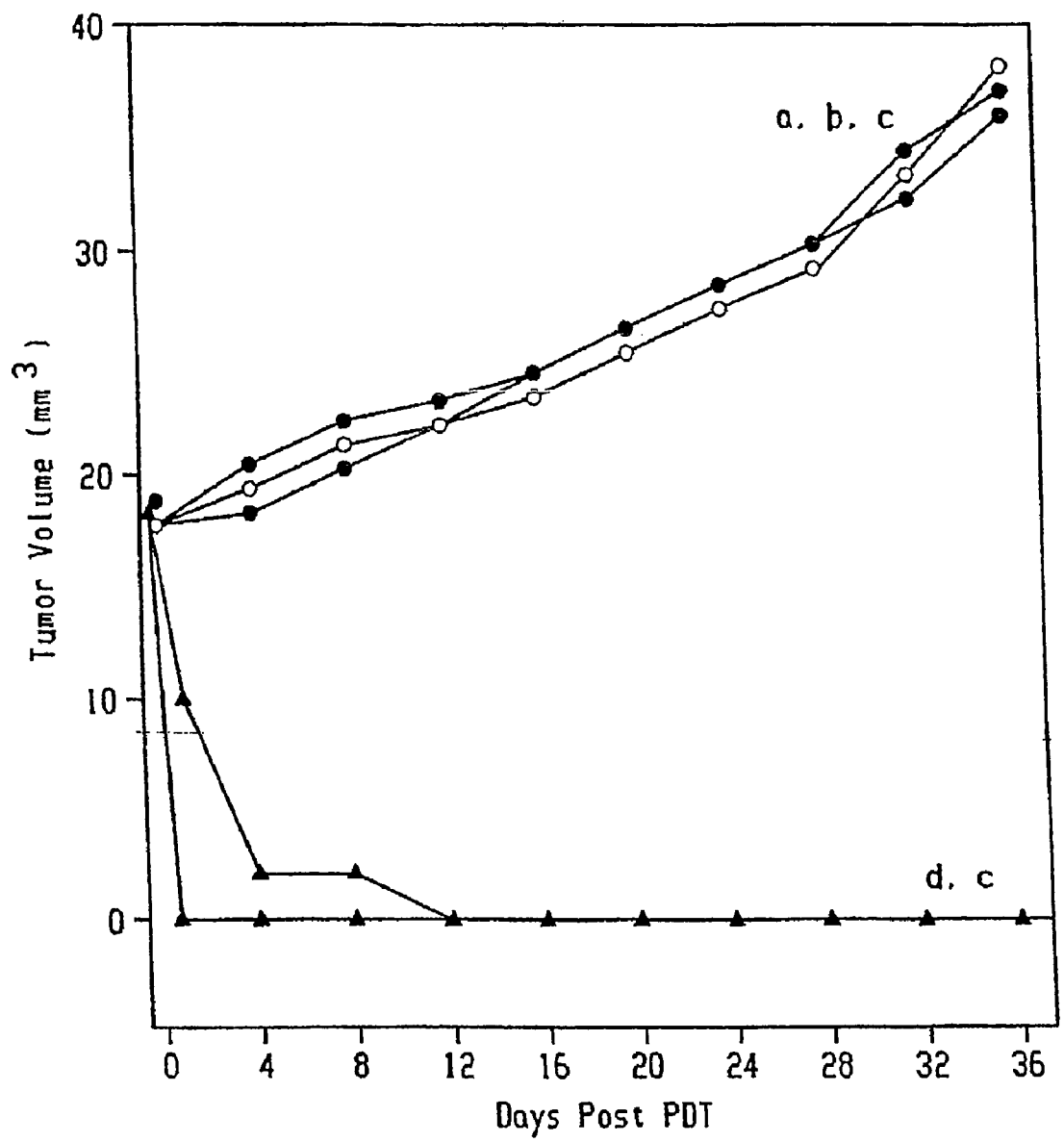
FIG. 4 shows the tumor volume response of chemically-induced benign skin papillomas in SENCAR mice, to photodynamic therapy with PcIV.

Curves for animals after PDT with Pc IV at the doses of 0.5 and 1.0 mg/kg are shown by d and e in FIG. 4. As shown in FIG. 4 the mice treated with PcIV and light showed a decrease in tumor volume which eventually decreased to 0 volume, that is, no tumor was measurable. The tumor did not return for the length of the study, 34 days. In contrast, the control tumor volume consistently increased over time.

Comparison of Uptake of PcIV and PcIV-Salts into Human Cancer Cells

The PcIV salts (PcIV-pyruvate and PcIV-hydrochloride) were compared to PcIV, with respect to their ability to be taken up into human breast cancer MCF-7c3 cells in vitro.

Figure 5:
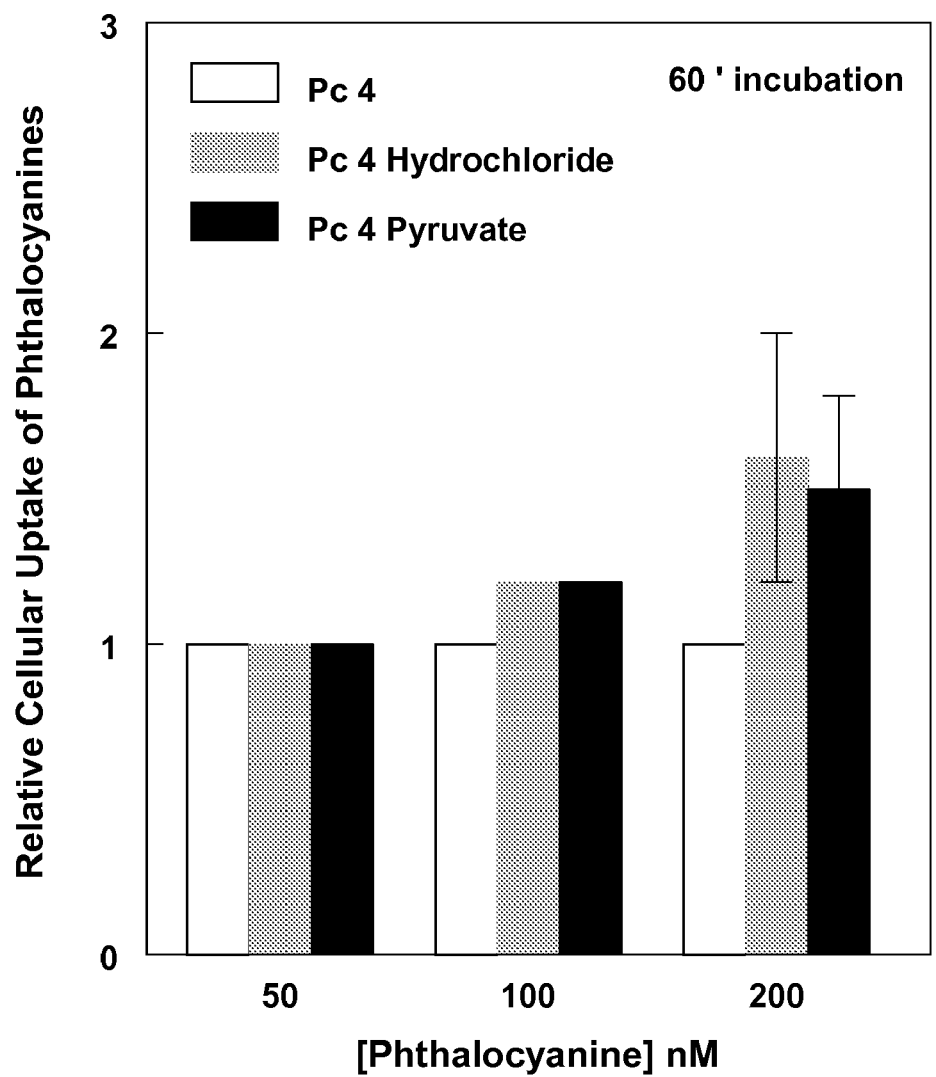
FIG. 5 is a graph which compares the relative cellular uptake of PcIV, PcIV hydrochloride, and PcIV pyruvate into human breast cancer MCF-7c3 cells in vitro.

Cells were grown in 5 mL of RPMI-1640 medium supplemented with 10% fetal calf serum in 60-mm diameter Petri dishes in a 37° C. incubator in an atmosphere of 5% $CO_2$, 95% air. Cultures were used when they were in exponential growth. For experiments, various concentrations (50, 100, or 200 nM) of each compound (PcIV, PcIV-HCl, PcIV-pyruvate), were added to the medium above the cells, and the dishes were returned to the incubator for 60 minutes to allow the photosensitizers to enter the cells. To evaluate uptake, the medium was removed, and the cells were detached from the plastic surface with trypsin and collected by centrifugation. The cell pellet was suspended in phenol-red-free Hank's balanced salt solution and analyzed by flow cytometry ($\lambda$ex=335-355 nm; emission collected through a 650-nm long-pass filter). For each cell sample, the data were expressed as the mean channel fluorescence and background was subtracted. Data for each concentration of the PcIV salts were then normalized to those for the same concentration of PcIV in the same experiment. In FIG. 5, data for 50 and 100 nM are single observations for each photosensitizer, whereas data for 200 nM are presented as the mean normalized values for three experiments. Error bars represent the standard deviation of the mean. The data show that the PcIV salts are at least as efficient, and possibly more efficient, in entering MCF-7c3 cells.

Successful Penetration of Topically-Applied PcIV and PcIV Salts into Human Skin

Human skin absorption of PcIV was analyzed by fluorescence confocal microscopy. PcIV fluorescence, upon activation with a HeNe laser at 633 nm, was visualized using a 650 long pass filter. Briefly, 0.4 mm thick human keratomes were removed from the gluteal region of healthy volunteers and divided into 1.5 cm×1.5 cm squares of skin. Upon application of PcIV to the epidermis in a vehicle of ethanol and propylene glycol, visualization of penetration of PcIV was achieved by fluorescence. Pc 4 was then prepared as PcIV-pyruvate and PcIV-HCl and applied in the same vehicle as Pc 4 to the epidermis. Three concentrations, namely, 0.1 mg/mL, 0.05 mg/mL, and 0.01 mg/mL were tested per PcIV formulation. Skin was incubated at 37° C. for 1, 2, and 4 hours, along with vehicle controls. Confocal analysis of each of the three formulations revealed PcIV fluorescence in membrane or peripheral cytoplasmic patterns on stratum granulosum keratinocytes with cytoplasmic pattern in the basal layer. Maximum PcIV fluorescence was detectable using laser transmission of 3% for the 0.1 mg/mL and 30% for the 0.01 mg/mL. Both PcIV.pyruvate and PcIV.HCl however could be visualized with a laser transmission of 2-3% for the 0.1 mg/mL and 7-9% for the 0.01 mg/mL concentrations. Because fluorescence was inversely proportional to the laser transmission at a constant laser gain, it was determined that PcIV successfully penetrated the skin to the basal layer in a dose dependent fashion, and that the salts may have enhanced penetration capacity for development as a topical PDT drug for topical applications.

Evaluation of the Penetration of Topically Applied PcIV and PcIV Salts into the Skin Via Confocal Fluorescence Microscopy The ability of PcIV and the newly prepared PcIV salts (HCl and pyruvate) to penetrate into the epidermis of keratome derived biopsies was examined. The time course of penetrance as well as the effect of dose of the PcIV compounds were evaluated. PcIV and the PcIV.HCl and PcIV.pyruvate salts were resuspended in ethanol (100%, 1 part PcIV, 499 parts ethanol) and then diluted to final concentrations in a 30% Propylene Glycol 70% Ethanol mixture.

Keratome biopsies of normal skin were obtained from normal volunteers after written consent according to UHHS IRB protocol # 05-95-03. To date, seven experiments have been performed. The range of age for volunteers was 20-40 yrs. Individuals represented Fitzpatrick skin types between I-III. Skin biopsies were held in PBS following the keratome procedure until processed for PcIV Application (less than 1 hr). The keratome skin samples (1.5 cm$^2$) were overlayed onto sterile gauze in 80 mm tissue culture petri dishes epidermal side down. PcIV compounds were then applied to the corners of the sterile gauze and allowed to "wick" through the gauze and contact the epidermis of the skin for the indicated times. Following the incubation, the tissue was removed from the gauze and washed three times in phosphate buffered saline and held, in PBS, until analysis by confocal microscopy. Confocal images were acquired using a 20×N.A. 0.5 water immersion objective on a Zeiss 510 confocal microscope. PcIV fluorescence was elicited using a 633 nm wavelength for excitation, and collected with a 633 nm dichroic mirror and 650 nm long-pass filter.

Figure 6A:
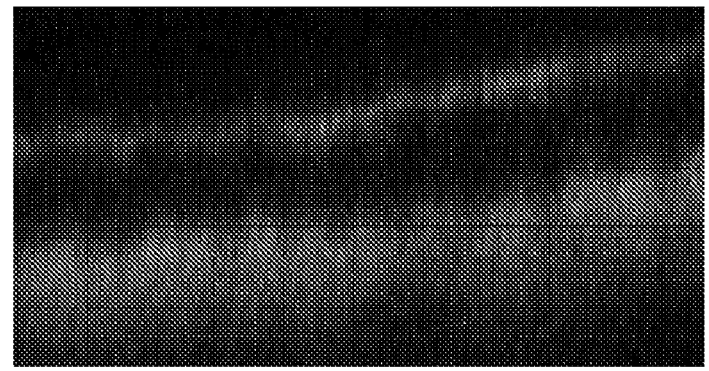
FIG. 6a is a confocal fluorescence image of PcIV in vertical cross section of human skin.
Figure 6B:
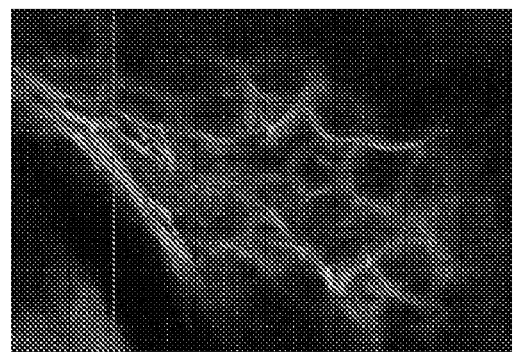
FIG. 6b is a confocal fluorescence image of PcIV in en face horizontal optical section of human skin.
Figure 6C:
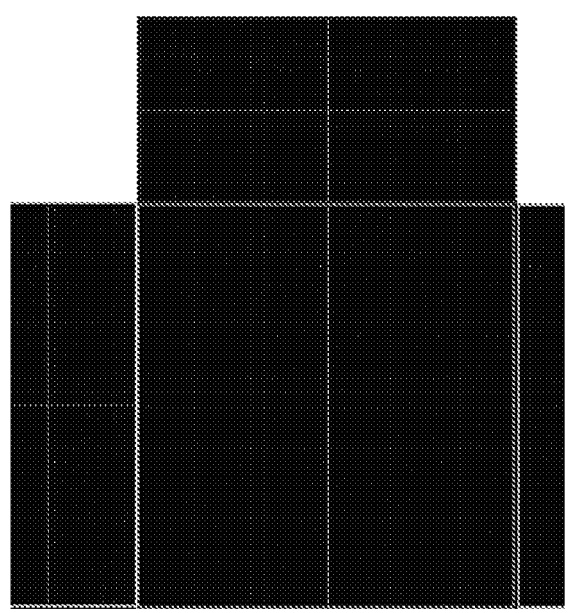
FIG. 6c is a confocal fluorescence image of a negative control of skin only plus exposure to vehicle.

Results: PcIV fluorescence shown in vertical cross section (FIG. 6*a*), and en face horizontal optical sections (FIG. 6*b*). PcIV fluorescence was measured 1 hr following application to the keratome biopsy. Negative control, skin only plus exposure to vehicle, showed no autofluorescence using this detection protocol (FIG. 6*c*)

Figure 7A:
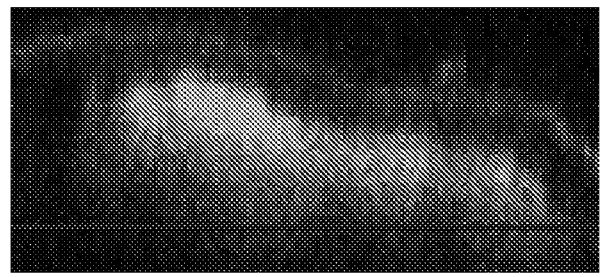
FIG. 7a shows a confocal fluorescence image of a confocal fluorescence image of a negative control of a keratome biopsy exposed to PcIV for 1 hour.
Figure 7B:
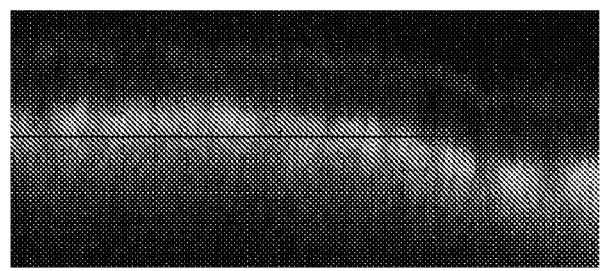
FIG. 7b shows a confocal fluorescence image of a keratome biopsy exposed to PcIV for 2 hours.
Figure 7C:
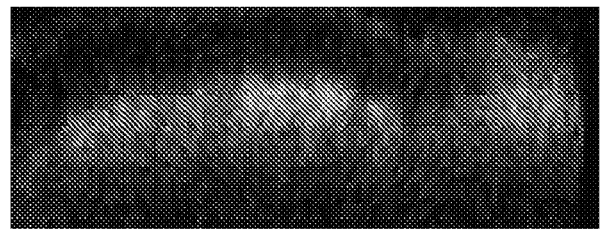
FIG. 7c shows a confocal fluorescence image of a keratome biopsy exposed to PcIV for 4 hours.
Figure 7D:
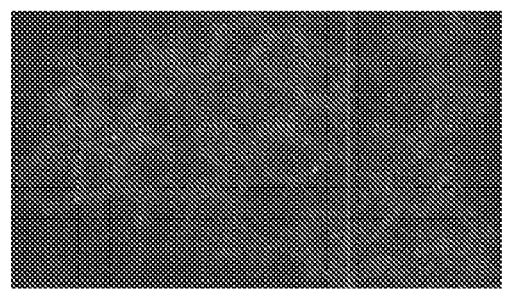
FIG. 7d shows a confocal fluorescence image of a cross-section of a keratome biopsy exposed to PcIV for 4 hours.

In order to assess the penetration of PcIV over time, a time course of PcIV uptake was evaluated. Keratome biopsies prepared as described above were exposed to PcIV for either 1 h (FIG. 7*a*), 2 h (FIG. 7*b*) or 4 h (FIG. 7*c*). A representative horizontal section (2 h) is also shown (FIG. 7*d*).

Figure 8A:
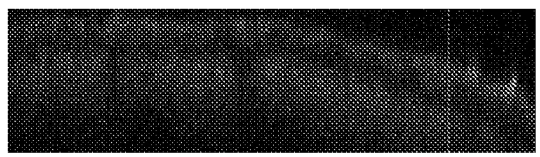
FIG. 8a shows a confocal fluorescence image of a keratome biopsy exposed to PcIV.
Figure 8B:
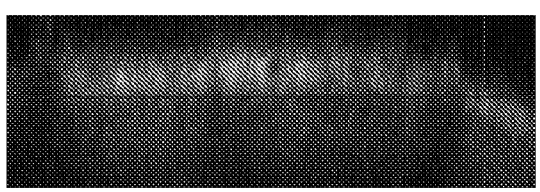
FIG. 8b shows a confocal fluorescence image of a keratome biopsy exposed to PcIV-pyruvate.
Figure 8C:
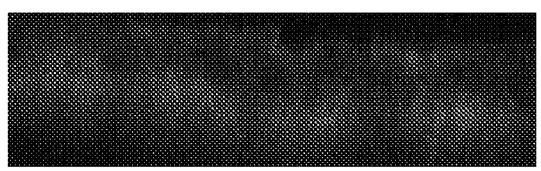
FIG. 8c shows a confocal fluorescence image of a keratome biopsy exposed to PcIV.HCl.
Figure 8D:
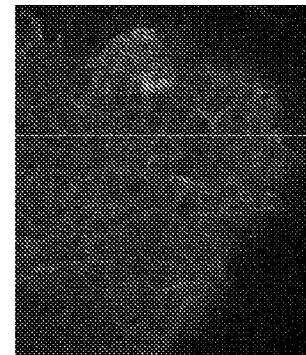
FIG. 8d shows a confocal fluorescence image of a cross section of a keratome biopsy exposed to PcIV.
Figure 8E:
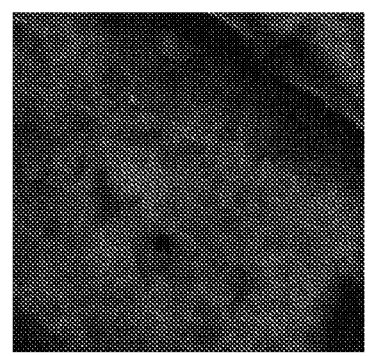
FIG. 8e shows a confocal fluorescence image of a cross section of a keratome biopsy exposed to PcIV.pyruvate.
Figure 8F:
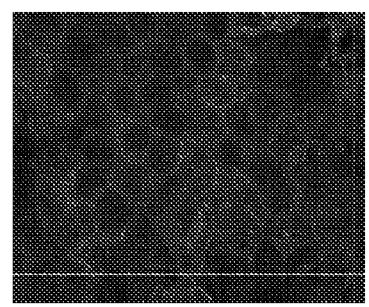
FIG. 8f shows a confocal fluorescence image of a cross section of a keratome biopsy exposed to PcIV.HCl.

Finally, the PcIV salts were compared to PcIV to assess uptake of the new compounds. PcIV (FIG. 8*a*) was compared to PcIV-pyruvate (FIG. 8*b*) and PcIV.HCl (FIG. 8*c*) for penetrating into the epidermis of keratome biopsies prepared as previously described. Cross sections of PcIV (FIG. 8*d*), PcIV-pyruvate (FIG. 8*e*) and PcIV.HCl (FIG. 8*f*) are also shown.

Figure 9:
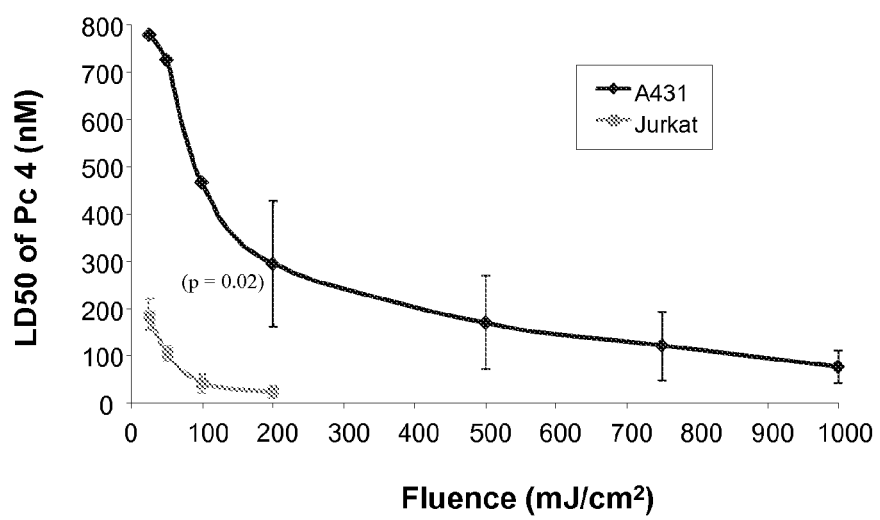
FIG. 9 shows a comparison of the sensitivity of Jurkat and A431 cells to PcIV-PDT, expressed as the amount of PcIV needed to cause a 50% decrease in survival at each indicated light dose. The data are derived from a series of individual dose-response curves.
Figure 10A:
FIG. 10a shows an untreated skin lesion.
Figure 10B:
FIG. 10b shows a TUNEL-positive area in the superficial epidermis seen 24 hours after PcIV-PDT treatment of a skin lesion.

In vitro PDT was performed by administration of a range of PCIV doses to the extracellular medium for 2 hours followed by irradiation with red light ($\lambda_{max}$=675 nm). After 24 hours, the cells were incubated in 3-(4,5-dimethylthiazol-2-dimthylthiazol-2-yl)-2,5-diphenyltetrazolium bromide (MTT) for 4 hours. Crystals formed by viable cells were dissolved in dimethylsulfoxide and the absorbance at 540 nm was measured. Cell viability was determined with reference to untreated cultures. The $LD_{50}$ was the concentration of PCIV that reduced viability to 50% of the control value at each indicated light fluence (FIG. 9).

Conclusion: effective penetration of PcIV through intact human stratum corneum is achieved within one hour. Penetration in the propylene glycol vehicle is demonstrated at the lowest concentration tested (0.01 mg/mL). Modifications of the PcIV compounds by formulation as a salt (PcIV.HCl) or (PcIV.pyruvate) does not hinder the penetration of the compound through the skin.

Treatment of Skin Conditions with PcIV

Eleven patients (nine males, two females) were treated with topical PcIV, wherein ten of these patients had a diagnosis of early mycosis fungoides at the patch/plaque stage. The remaining patient had a diagnosis of squamous cell carcinoma. PcIV solution concentrations were either 0.01 mg/mL or 0.05 mg/mL. One hour after administration of the PcIV solution, the skin lesions were exposed to a 675 nm laser, dose ranging from 50-100 J/$cm^2$. No significant adverse effects were observed during the treatment. Two patients felt some heat over the treatment site during the first few minutes of laser exposure. No adverse reactions were seen for the entire observation period, which was up to two weeks post treatment. Because Pc 4 is a photosensitizer, individual patient sun sensitivity was monitored by serial phototesting using solar simulated radiation. No significant changes were observed in the patients' sunburn threshold or their minimum erythema dose (MED). No cures have been achieved to date. Two patients showed a minimal decrease in erythema and infiltration of their lesions. In one patient who showed some clinical response, lesional skin biopsies performed 24 hours after treatment showed an increase in TUNEL positivity along the superficial portion of the lesion. TUNEL positivity was not demonstrated in adjacent lesional skin that was not treated with PcIV PDT. (see FIGS. 10*a* and 10*b*).

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

The invention claimed is:

1. A pharmaceutical composition for topical administration, comprising a phthalocyanine that has a structure of formula (II) or a pharmaceutically acceptable salt thereof, and a pharmaceutically acceptable carrier, (II)

wherein M is $(G)_aY[(OSi(CH_3)_2(CH_2)_bN_c(R')_d(R'')_e)_f X_g]_p$;

Y is selected from Si, Al, Ga, Ge, or Sn;

R' is selected from H, $CH_3$, $C_2H_5$, $C_4H_9$, $C_4H_8NH$, $C_4H_8N$, $C_4H_8NCH_3$, $C_4H_8S$, $C_4H_8O$, $C_4H_8Se$, $OC(O)CH_3$, OC(O), CS, CO, CSe, OH, $C_4H_8N(CH_2)_3CH_3$, $(CH_2)_2N(CH_3)_2$, $(CH_2)_nN((CH_2)_o(CH_3))_2$, and an alkyl group having from 1 to 12 carbon atoms;

R'' is selected from H, $SO_2CH_3$, $(CH_2)_2N(CH_3)_2$, $(CH_2)_{11}CH_3$, $C(S)NHC_6H_{11}O_5$, $(CH_2)_nN((CH_2)_o(CH_3))_2$, and an alkyl group having from 1 to 12 carbon atoms;

G is selected from OH and $CH_3$;

X is selected from hydrobromide, hydrochloride, sulfate, bisulfate, phosphate, nitrate, acetate, pyruvate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate forming anions;

a is 0 or 1;

b is an integer from 2 to 12;

c is 0 or 1;

d is an integer from 0 to 3;

e is an integer from 0 to 2;

f is 1 or 2;

g is 0 or 1;

n is an integer from 1 to 12;

o is an integer from 1 to 11;

p is 1 or 2

$R^1$-$R^{16}$ are each independently selected from hydrogen, halogen, nitro, cyano, hydroxy, thiol, amino, carboxy, aryl, heteroaryl, carbocyclyl, heterocyclyl, $C_{1-20}$alkyl, $C_{1-20}$alkenyl, $C_{1-20}$alkynyl, $C_{1-20}$alkoxy, $C_{1-20}$acyl, $C_{1-20}$alkylcarbonyloxy, $C_{1-20}$aralkyl, $C_{1-20}$hetaralkyl, $C_{1-20}$carbocyclylalkyl, $C_{1-20}$heterocyclylakl, $C_{1-20}$aminoalkyl, $C_{1-20}$alkylamino, $C_{1-20}$thioalkyl, $C_{1-20}$alicylthio, $C_{1-20}$hydroxyalkyl, $C_{1-20}$alkyloxycarbonyl, $C_{1-20}$alkylaminocarbonyl, $C_{1-20}$alkylcarbonylamino, $C_{1-20}$alkyl-Z—$C_{1-10}$alkyl;

$R^{17}$ is selected from hydrogen, $C_{1-20}$acyl, $C_{1-20}$alkyl, and $C_{1-20}$aralkyl; and Z is selected from S, $NR^{17}$, and O.

2. The pharmaceutical composition of claim 1, wherein $R^1$-$R^{16}$ are hydrogen.

3. A pharmaceutical composition of claim 2, wherein M is selected from $AlOSi(CH_3)_2(CH_2)_3N(CH_3)_2$; $AlOSi(CH_3)_2(CH_2)_3N(CH_3)_3{}^+I^-$; $CH_3SiOSi(CH_3)_2(CH_2)_3N(CH_3)_2$; $HOSiOSi(CH_3)_2(CH_2)_3N(CH_3)_2$; $HOSiOSi(CH_3)_2(CH_2)_3N(CH_3)_3{}^+I^-$; $Si[OSi(CH_3)_2(CH_2)_3N(CH_3)_3{}^+I^-]_2$; $Si[OSi(CH_3)_2(CH_2)_4NH_2]_2$; $Si[OSi(CH_3)_2(CH_2)_4NHSO_2CH_3]_2$; $HOSiOSi(CH_3)_2(CH_2)_4NHSO_2CH_3$; $HOSiOSi(CH_3)_2(CH_2)_3N(CH_2CH_3)(CH_2)_2N(CH_3)_2$; $Si[OSi(CH_3)_2(CH_2)_4NHCSNHC_6H_{11}O_5]_2$; $Si[OSi(CH_3)_2(CH_2)_3N(CH_3)_2]_2$; $HOSiOSi(CH_3)_2(CH_2)_3OCOCH_3$; $HOSiOSi(CH_3)_2(CH_2)_3OH$; $Si[OSi(CH_3)_2(CH_2)_3N(CH_2CH_3)(CH_2)_2N(CH_3)_2]_2$; $HOSiOSi(CH_3)_2(CH_2)_3NC_4H_8O$; $AlOSi(CH_3)_2(CH_2)_3N^+(CH_3)_2(CH_2)_{11}CH_3I^-$; $HOSiOSi(CH_3)_2(CH_2)_8N(CH_3)_2$; $Si[OSi(CH_3)_2(CH_2)_3NC_4H_8O]_2$; $HOSiOSi(CH_3)_2(CH_2)_3NC_4H_8S$; $HOSiOSi(CH_3)_2(CH_2)_3N(CH_2)_3(CH_3)_2$; $HOSiOSi(CH_3)_2(CH_2)_3NCS$; $HOSiOSi(CH_3)_2(CH_2)_3N[(CH_2)_3N(CH_3)_2]_2$; $HOSiOSi(CH_3)_2(CH_2)_3NC_4H_8NCH_3$; $Si[OSi(CH_3)_2(CH_2)_3NC_4H_8NCH_3]_2$; $HOSiOSi(CH_3)_2(CH_2)_3NC_4H_8N(CH_2)_3CH_3$; and $Si[OSi(CH_3)_2(CH_2)_3NC_4H_8NH]_2$.

4. A pharmaceutical composition of claim 3, wherein M is $HOSiOSi(CH_3)_2(CH_2)_3N(CH_3)_2$.

5. A pharmaceutical composition of claim 1, wherein the phthalocyanine is formulated as a salt selected from hydrochloride and pyruvate.

6. A pharmaceutical composition of claim 5, wherein the phthalocyanine is formulated as a hydrochloride salt.

7. A pharmaceutical composition of claim 6, wherein the phthalocyanine is formulated as a pyruvate salt.

8. A method for treating epithelial cancer or other epithelial cell abnormalities, comprising
(i) topically administering a phthalocyanine pharmaceutical composition to an epithelial surface; and
(ii) irradiating the epithelial surface,
wherein the phthalocyanine has a structure of formula (II) or a pharmaceutically acceptable salt thereof

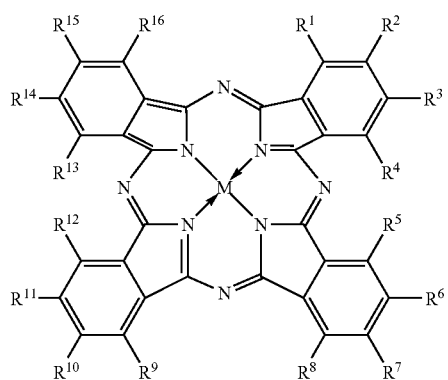

(II)

wherein M is $(G)_a Y[(OSi(CH_3)_2(CH_2)_b N_c(R')_d(R'')_e)_f X_g]_p$;

Y is selected from Si, Al, Ga, Ge, or Sn;

R' is selected from H, $CH_3$, $C_2H_5$, $C_4H_9$, $C_4H_8NH$, $C_4H_8N$, $C_4H_8NCH_3$, $C_4H_8S$, $C_4H_8O$, $C_4H_8Se$, $OC(O)CH_3$, $OC(O)$, $CS$, $CO$, $CSe$, $OH$, $C_4H_8N(CH_2)_3CH_3$, $(CH_2)_2N(CH_3)_2$, $(CH_2)_nN((CH_2)_o(CH_3))_2$, and an alkyl group having from 1 to 12 carbon atoms;

R" is selected from H, $SO_2CH_3$, $(CH_2)_2N(CH_3)_2$, $(CH_2)_{11}CH_3$, $C(S)NHC_6H_{11}O_5$, $(CH_2)_nN((CH_2)_o(CH_3))_2$, and an alkyl group having from 1 to 12 carbon atoms;

G is selected from OH and $CH_3$;

X is selected from hydrobromide, hydrochloride, sulfate, bisulfate, phosphate, nitrate, acetate, pyruvate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate forming anions;

a is 0 or 1;
b is an integer from 2 to 12;
c is 0 or 1;
d is an integer from 0 to 3;
e is an integer from 0 to 2;
f is 1 or 2;
g is 0 or 1;
n is an integer from 1 to 12;
o is an integer from 1 to 11;
p is 1 or 2;

$R^1$-$R^6$ are each independently selected from hydrogen, halogen, nitro, cyano, hydroxy, thiol, amino, carboxy, aryl, heteroaryl, carbocyclyl, heterocyclyl, $C_{1-20}$alkenyl, $C_{1-20}$alkynyl, $C_{1-20}$alkoxy, $C_{1-20}$acyl, $C_{1-20}$alkylcylcarbonyloxy, $C_{1-20}$aralkyl, $C_{1-20}$hetaralkyl, $C_{1-20}$carbocyclylalkyl, $C_{1-20}$heterocyclylalkyl, $C_{1-20}$aminoalkyl, $C_{1-20}$alkylamino, $C_{1-20}$thioalkyl, $C_{1-20}$alkylthio, $C_{1-20}$hydroxyalkyl, $C_{1-20}$alkyloxycarbonyl, $C_{1-20}$alkylaminocarbonyl, $C_{1-20}$alkylcarbonylamino, $C_{1-10}$alkyl-Z—$C_{1-10}$alkyl;

$R^{17}$ is selected from hydrogen, $C_{1-20}$acyl, $C_{1-20}$alkyl, and $C_{1-20}$aralkyl; and Z is selected from S, $NR^{17}$, and O.

9. The method of claim 8, wherein $R^1$-$R^{16}$ are hydrogen.

10. A method of claim 9, wherein M is selected from $AlOSi(CH_3)_2(CH_2)_3N(CH_3)_2$; $AlOSi(CH_3)_2(CH_2)_3N(CH_3)_3^+I^-$; $CH_3SiOSi(CH_3)_2(CH_2)_3N(CH_3)_2$; $OSiOSi(CH_3)_2(CH_2)_3N(CH_3)_2$; $HOSiOSi(CH_3)_2(CH_2)_3N(CH_3)_3^+I^-$; $Si[OSi(CH_3)_2(CH_2)_3N(CH_3)_3^+I^-]_2$; $Si[OSi(CH_3)_2(CH_2)_4NH_2]_2$; $Si[OSi(CH_3)_2(CH_2)_4NHSO_2CH_3]_2$; $HOSiOSi(CH_3)_2(CH_2)_4NHSO_2CH_3$; $HOSiOSi(CH_3)_2(CH_2)_3N(CH_2CH_3)(CH_2)_2N(CH_3)_2$; $Si[OSi(CH_3)_2(CH_2)_4NHCSNHC_6H_{11}O_5]_2$; $Si[OSi(CH_3)_2(CH_2)_3N(CH_3)_2]_2$; $HOSiOSi(CH_3)_2(CH_2)_3OCOCH_3$; $HOSiOSi(CH_3)_2(CH_2)_3OH$; $Si[OSi(CH_3)_2(CH_2)_3N(CH_2CH_3)(CH_2)_2N(CH_3)_2]_2$; $HOSiOSi(CH_3)_2(CH_2)_3NC_4H_8O$; $AlOSi(CH_3)_2(CH_2)_3N^+(CH_3)_2(CH_2)_{11}CH_3I^-$; $HOSiOSi(CH_3)_2(CH_2)_8N(CH_3)_2$; $Si[OSi(CH_3)_2(CH_2)_3NC_4H_8O]_2$; $HOSiOSi(CH_3)_2(CH_2)_3NC_4H_8S$; $HOSiOSi(CH_3)_2(CH_2)_3N(CH_2)_3(CH_3)_2$; $HOSiOSi(CH_3)_2(CH_2)_3NCS$; $HOSiOSi(CH_3)_2(CH_2)_3N[(CH_2)_2N(CH_3)_2]_2$; $HOSiOSi(CH_3)_2(CH_2)_3NC_4H_8NCH_3$; $Si[OSi(CH_3)_2(CH_2)_3NC_4H_8NCH_3]_2$; $HOSiOSi(CH_3)_2(CH_2)_3NC_4H_8N(CH_2)_3CH_3$; and $Si[OSi(CH_3)_2(CH_2)_3NC_4H_8NH]_2$.

11. A method of claim 10, wherein M is $HOSiOSi(CH_3)_2(CH_2)_3N(CH_3)_2$.

12. A method of claim 8, wherein the phthalocyanine is formulated as a salt selected from hydrochloride and pyruvate.

13. The method of claim 12, wherein the phthalocyanine is formulated as a hydrochloride salt.

14. A method of claim 12, wherein the phthalocyanine is formulated as a pyruvate salt.

15. A pharmaceutically acceptable salt of a compound having a structure of formula (II)

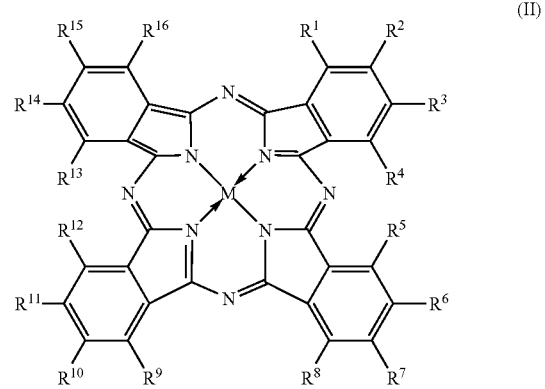

(II)

wherein M is $(G)_a Y[(OSi(CH_3)_2(CH_2)_b N_c(R')_d(R'')_e)_f X_g]_p$;

Y is selected from Si, Al, Ga, Ge, or Sn;

R' is selected from H, $CH_3$, $C_2H_5$, $C_4H_9$, $C_4H_8NH$, $C_4H_8N$, $C_4H_8NCH_3$, $C_4H_8S$, $C_4H_8O$, $C_4H_8Se$, $OC(O)CH_3$, $OC(O)$, $CS$, $CO$, $CSe$, $OH$, $C_4H_8N(CH_2)_3CH_3$, $(CH_2)_2N(CH_3)_2$, $(CH_2)_nN((CH_2)_o(CH_3))_2$, and an alkyl group having from 1 to 12 carbon atoms;

R" is selected from H, $SO_2CH_3$, $(CH_2)_2N(CH_3)_2$, $(CH_2)_{11}CH_3$, $C(S)NHC_6H_{11}O_5$, $(CH_2)_nN((CH_2)_o(CH_3))_2$, and an alkyl group having from 1 to 12 carbon atoms;

G is selected from OH and $CH_3$;

X is selected from hydrobromide, hydrochloride, sulfate, bisulfate, phosphate, nitrate, acetate, pyruvate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate forming anions;

a is 0 or 1;
b is an integer from 2 to 12;
c is 0 or 1;
d is an integer from 0 to 3;
e is an integer from 0 to 2;
f is 1 or 2;
g is 0 or 1;
n is an integer from 1 to 12;
o is an integer from 1 to 11; and
p is 1 or 2; and
$R^1$-$R^{16}$ are each independently selected from hydrogen, halogen, nitro, cyano, hydroxy, thiol, amino, carboxy, aryl, heteroaryl, carbocyclyl, heterocyclyl, $C_{1-20}$alkyl, $C_{1-20}$alkenyl, $C_{1-20}$alkynyl, $C_{1-20}$alkoxy, $C_{1-20}$acyl, $C_{1-20}$alkylcarbonyloxy, $C_{1-20}$aralkyl, $C_{1-20}$hetaralkyl, $C_{1-20}$carbocyclylalkyl, $C_{1-20}$heterocyclylalkyl, $C_{1-20}$aminoalkyl, $C_{1-20}$alkylamino, $C_{1-20}$thioalkyl, $C_{1-20}$malkylthio, $C_{1-20}$hydroxyalkyl, $C_{1-20}$alkyloxycarbonyl, $C_{1-20}$alkylaminocarbonyl, $C_{1-20}$malkylcarbonylamino, $C_{1-20}$alkyl-Z-$C_{1-10}$alkyl;
$R^{17}$ is selected from hydrogen, $C_{1-20}$acyl, $C_{1-20}$alkyl, and $C_{1-20}$aralkyl; and
Z is selected from S, $NR^{17}$, and O.

16. The pharmaceutically acceptable salt of claim 15 wherein $R^1$-$R^{16}$ are hydrogen.

17. The pharmaceutically acceptable salt of claim 16, wherein M is selected from $AlOSi(CH_3)_2(CH_2)_3N(CH_3)_2$; $AlOSi(CH_3)_2(CH_2)_3N(CH_3)_3{}^+I^-$; $CH_3SiOSi(CH_3)_2(CH_2)_3N(CH_3)_2$; $HOSiOSi(CH_3)_2(CH_2)_3N(CH_3)_2$; $HOSiOSi(CH_3)_2(CH_2)_3N(CH_3)_3{}^+I^-$; $Si[OSi(CH_3)_2(CH_2)_3N(CH_3)_3{}^+I^-]_2$; $Si[OSi(CH_3)_2(CH_2)_4NH_2]_2$; $Si[OSi(CH_3)_2(CH_2)_4NHSO_2CH_3]_2$; $HOSiOSi(CH_3)_2(CH_2)_4NHSO_2CH_3$; $HOSiOSi(CH_3)_2(CH_2)_3N(CH_2CH_3)(CH_2)_2N(CH_3)_2$; $Si[OSi(CH_3)_2(CH_2)_4NHCSNHC_6H_{11}O_5]_2$; $Si[OSi(CH_3)_2(CH_2)_3N(CH_3)_2]_2$; $HOSiOSi(CH_3)_2(CH_2)_3OCOCH_3$; $HOSiOSi(CH_3)_2(CH_2)_3OH$; $Si[OSi(CH_3)_2(CH_2)_3N(CH_2CH_3)(CH_2)_2N(CH_3)_2]_2$; $HOSiOSi(CH_3)_2(CH_2)NC_4H_8O$; $AlOSi(CH_3)_2(CH_2)_3N^+(CH_3)_2(CH_2)_{11}CH_3I^-$; $HOSiOSi(CH_3)_2(CH_2)_8N(CH_3)_2$; $Si[OSi(CH_3)_2(CH_2)_3NC_4H_8O]_2$; $HOSiOSi(CH_3)_2(CH_2)_3NC_4H_8S$; $HOSiOSi(CH_3)_2(CH_2)_3N(CH_2)_3(CH_3)_2$; $HOSiOSi(CH_3)_2(CH_2)_3NCS$; $HOSiOSi(CH_3)_2(CH_2)_3N[(CH_2)_3N(CH_3)_2]_2$; $HOSiOSi(CH_3)_2(CH_2)_3NC_4H_8NCH_3$; $Si[OSi(CH_3)_2(CH_2)_3NC_4H_8NCH_3]_2$; $HOSiOSi(CH_3)_2(CH_2)_3NC_4H_8N(CH_2)_3CH_3$; and $Si[OSi(CH_3)_2(CH_2)_3NC_4H_8NH]_2$.

18. The pharmaceutically acceptable salt of claim 17, wherein M is $HOSiOSi(CH_3)_2(CH_2)_3N(CH_3)_2$.

19. The salt of claim 15, wherein the salt is the hydrochloric salt.

20. The salt of claim 15, wherein the salt is the pyruvate salt.

* * * * *